(12) United States Patent
Ariyasu et al.

(10) Patent No.: US 7,098,026 B1
(45) Date of Patent: Aug. 29, 2006

(54) HUMAN DESERT HEDGEHOG PROTEIN

(75) Inventors: Toshio Ariyasu, Okayama (JP); Shuji Nakamura, Okayama (JP); Kunzo Orita, Okayama (JP)

(73) Assignee: Kabushiki Kaisha Hayashibara Seibutsu Kagaku Kenkyujo, Okayama (JP)

(*) Notice: Subject to any disclaimer, the term of this patent is extended or adjusted under 35 U.S.C. 154(b) by 626 days.

(21) Appl. No.: 09/617,545

(22) Filed: Jul. 14, 2000

Related U.S. Application Data

(62) Division of application No. 09/063,778, filed on Apr. 22, 1998.

(30) Foreign Application Priority Data

Apr. 25, 1997 (JP) .............................................. 9-121578
Apr. 14, 1998 (JP) ........................................... 10/117873

(51) Int. Cl.
*C12N 5/00* (2006.01)

(52) U.S. Cl. .................... 435/325; 435/69.1; 435/252.3; 435/254.11; 536/23.1; 536/23.5; 530/350; 530/412; 530/413; 530/414; 530/416; 530/417; 530/418; 530/422

(58) Field of Classification Search ................ 536/23.1, 536/23.5; 435/69.1, 320.1, 325, 252.3, 254.11, 435/240, 468; 530/300, 350, 402, 412–422; 800/2, 9, 13
See application file for complete search history.

(56) References Cited

U.S. PATENT DOCUMENTS

| 5,759,811 A | 6/1998 | Epstein et al. |
| 5,789,543 A | * 8/1998 | Ingham et al. |
| 5,844,079 A | 12/1998 | Ingham et al. |
| 5,955,595 A | 9/1999 | Korsmeyer |

FOREIGN PATENT DOCUMENTS

| EP | 0 658 627 A2 | 6/1995 |
| JP | 7 163368 | 6/1995 |
| WO | 95 18856 | 7/1995 |
| WO | 95 23223 | 8/1995 |

OTHER PUBLICATIONS

Reeck et al., Cell, 50:667, Aug. 28, 1987.*
Drummond, I.A., GenBank Accession No. U59748, "Human desert hedgehog (hDHH) mRNA, partial cds.", Jul. 3, 1996.*
Bitgood et al., Sertoli cell signaling by Desert hedgehog regulates the male germline, Current Biol. 6(3):298–304 (1996).*

Krauss et al., A functionally conserved homolog of the drosophila segment polarity gene hh is expressed in tissues with polarizing activity in zebrafish embryos, Cell 75: 1431–1441 (Dec. 31, 1993).*
Echelard et al., Sonice hedgehog, a member of a family of putative signaling moelcules, is implicated in the regulation of CNS polarity, Cell 75:1417–1430 (Dec. 31, 1993).*
Nusslein–Volhard, C. et al., "Mutations Affecting Segment Number and Polarity in Drosophila," *Nature*, 287:795–801 (1980).
Lee, J. J. et al., "Secretion and Localized Transcription Suggest a Role in Positional Signaling for Products of the Segmentation Gene hedgehog," *Cell*, 71:33–50 (1992).
Echelard, Y. et al., "Sonic Hedgehog, a Member of a Family of Putative Signaling Molecules, Is Implicated in the Regulation of CNS Polarity," *Cell*, 75:1417–1430 (1993).
Marigo, V. et al., "Cloning, Expression, and Chromosomal Location of SHH and IHH: Two Human Homologues of the Drosophila Segment Polarity Gene Hedehog," *Genomics*, 28:44–51 (1995).
The nucleotide sequence of mouse Desert hedgehog gene registered under the accession No. "X76292" in "GenBank," a nucleic acid database by National Institute of Health, USA.
Kishi, K. "A New Leukemia Cell Line with Philadelphia Chromsome Characterized as Basophil Precursors," *Leukemia Research*, 9:381–390 (1985).
Jikken–Igaku–Bessatsu, Saibo–Kogaku Handbook (The handbook for the cell engineering), edited by Toshio Kuroki, Masaru Taniguchi and Mitsuo Oshimura, published by Yodosha Co. Ltd., Tokyo, Japan (1992).
Jikken–Igaku–Bessatsu, Biomanual Series 3, Idenshi–Cloning–Hikken–Ho (The experimental methods for the gene cloning), edited by Takashi Tokota and Kenichi Arai, published by Yodosha Co., Ltd., Tokyo, Japan (1993).
Jikken–Igaku–Bessatsu, Shin–Idenshikogaku–Handbook (The Handbook for Genetic Engineering), edited by Masami Muramatsu, Hiroto Okayama, and Tadashi Yamamoto, published by Yodosha Co., Ltd., Tokyo, Japan 269–283 (1996).

(Continued)

*Primary Examiner*—Lorraine Spector
*Assistant Examiner*—Claire M. Kaufman
(74) *Attorney, Agent, or Firm*—Browdy and Neimark, P.L.L.C.

(57) ABSTRACT

Disclosed are a novel hedgehog protein, i.e., a Desert hedgehog protein of human origin including mature and precursor forms, a DNA encoding the protein, a monoclonal antibody recognizing the protein, a process for producing the protein, and a method for detecting the protein. The hedgehog protein is useful in establishment of hybridomas which produce antibodies recognizing the protein, and the monoclonal antibody is useful in detection and purification of the protein. The hedgehog protein, DNA, and monoclonal antibody of this invention have efficacy in elucidation of hereditary morphological abnormalities in humans to establish their treatments and diagnoses.

12 Claims, 3 Drawing Sheets

OTHER PUBLICATIONS

Tan–Clone–Kotai–Manual (Experiemental Manual for Monoclonal Antibody), edited by Sakuji Toyama and Tamie Ando, published by Kodansha Scientific, Ltd., Tokyo, Japan, 105–152 (1991).

P. Tijssen, Enzyme Immunoassay (Practice and Theory of Enzyme Immunoassays), translated by Eiji Ishikawa, published by Tokyo–Kagaku–Dojin, Tokyo, Japan, 196–348 (1989).

Jikken–Igaku–Bessatsu, Biomanual UP Series, Idenshichiryo–no–Kisogijutsu (Basic techniques for the gene therapy), edited by Takashi Shimada, Izumi Saito, and Keiya Ozawa, published by Yodosha Co., Ltd., Tokyo, Japan (1996).

Hammerschmidt, M. et al., "The World According to Hedgehog," *Trends in Genetics*, 13:14–21 (1997).

The nucleotide sequence registered under the accession No. "AA064660" in "GenBank," a nucleic acid database by National Institute of Health, USA.

DNA cloning, vol. 1, edited by D. M. Glover, published by IRL press limited, Oxford, England (1985), pp. 109–136.

Laemli, U. K., "Cleavage of Structural Proteins during the Assembly of the Head of Bacteriophage T4," *Nature*, 227:680–685 (1970).

The nucleotide sequence of a human Sonic hedgehog gene, reported by V. Marigo et al. and registered under the accession No. "L38518" in "GenBank," a nucleic acid database by National Institute of Health, USA.

ATCC Cell Lines and Hybridomas, Eighth Edition, 1994, edited by Robert Hey, PH.D., et al., published by American Type Culture Collection, Rockvill, Maryland, USA (1994), pagrs describing the cell lines referred to in the specification.

Abstract of XP 002079893, Drumond, "Human Desert Hedgehog", (1996).

Tate et al, GenBank Accession No. AB010994, "Human Desert Hedgehog Third Exon", Feb. 14, 1998.

* cited by examiner

Note: On Lane 1, human Desert hedgehog protein was electrophoresed. On Lane 2, human Sonic hedgehog protein was electrophoresed. Numbers on left side of each lane mean the molecular weights of molecular weight markers in a unit of kilodaltons and indicate their positions after electrophoresis.

Note: Closed circles represent the results of detecting human Desert hedgehog protein, and closed squares represent the results of detecting human Sonic hedgehog protein.

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
      (A) LENGTH: 176 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Cys Gly Pro Gly Arg Gly Pro Val Gly Arg Arg Arg Tyr Ala Arg Lys
 1               5                  10                  15

Gln Leu Val Pro Leu Leu Tyr Lys Gln Phe Val Pro Gly Val Pro Glu
            20                  25                  30

Arg Thr Leu Gly Ala Ser Gly Pro Ala Glu Gly Arg Val Ala Arg Gly
            35                  40                  45

Ser Glu Arg Phe Arg Asp Leu Val Pro Asn Tyr Asn Pro Asp Ile Ile
        50                  55                  60

Phe Lys Asp Glu Glu Asn Ser Gly Ala Asp Arg Leu Met Thr Glu Arg
 65                 70                  75                  80

Cys Lys Glu Arg Val Asn Ala Leu Ala Ile Ala Val Met Asn Met Trp
                85                  90                  95

Pro Gly Val Arg Leu Arg Val Thr Glu Gly Trp Asp Glu Asp Gly His
                100                 105                 110

His Ala Gln Asp Ser Leu His Tyr Glu Gly Arg Ala Leu Asp Ile Thr
            115                 120                 125

Thr Ser Asp Arg Asp Arg Asn Lys Tyr Gly Leu Leu Ala Arg Leu Ala
            130                 135                 140

Val Glu Ala Gly Phe Asp Trp Val Tyr Tyr Glu Ser Arg Asn His Ile
145                 150                 155                 160

His Val Ser Val Lys Ala Asp Asn Ser Leu Ala Val Arg Ala Gly Gly
                165                 170                 175
```

(2) INFORMATION FOR SEQ ID NO: 2:

(i) SEQUENCE CHARACTERISTICS:
      (A) LENGTH: 374 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: mat peptide
      (B) LOCATION: 1..176
      (C) IDENTIFICATION METHOD: S (xi) SEQUENCE DESCRIPTION: SEQ ID NO: 2:

```
Cys Gly Pro Gly Arg Gly Pro Val Gly Arg Arg Arg Tyr Ala Arg Lys
 1               5                  10                  15
```

```
Gln Leu Val Pro Leu Leu Tyr Lys Gln Phe Val Pro Gly Val Pro Glu
             20                  25                  30

Arg Thr Leu Gly Ala Ser Gly Pro Ala Glu Gly Arg Val Ala Arg Gly
         35                  40                  45

Ser Glu Arg Phe Arg Asp Leu Val Pro Asn Tyr Asn Pro Asp Ile Ile
     50                  55                  60

Phe Lys Asp Glu Glu Asn Ser Gly Ala Asp Arg Leu Met Thr Glu Arg
 65                  70                  75                  80

Cys Lys Glu Arg Val Asn Ala Leu Ala Ile Ala Val Met Asn Met Trp
             85                  90                  95

Pro Gly Val Arg Leu Arg Val Thr Glu Gly Trp Asp Glu Asp Gly His
            100                 105                 110

His Ala Gln Asp Ser Leu His Tyr Glu Gly Arg Ala Leu Asp Ile Thr
            115                 120                 125

Thr Ser Asp Arg Asp Arg Asn Lys Tyr Gly Leu Leu Ala Arg Leu Ala
        130                 135                 140

Val Glu Ala Gly Phe Asp Trp Val Tyr Tyr Glu Ser Arg Asn His Ile
145                 150                 155                 160

His Val Ser Val Lys Ala Asp Asn Ser Leu Ala Val Arg Ala Gly Gly
                165                 170                 175

Cys Phe Pro Gly Asn Ala Thr Val Arg Leu Trp Ser Gly Glu Arg Lys
            180                 185                 190

Gly Leu Arg Glu Leu His Arg Gly Asp Trp Val Leu Thr Ala Asp Ala
        195                 200                 205

Ser Gly Arg Val Val Pro Thr Pro Val Leu Leu Phe Leu Asp Arg Asp
    210                 215                 220

Leu Gln Arg Arg Ala Ser Phe Val Ala Val Glu Thr Glu Trp Pro Pro
225                 230                 235                 240

Arg Lys Leu Leu Leu Thr Pro Trp His Leu Val Phe Ala Ala Arg Gly
                245                 250                 255

Pro Ala Pro Ala Pro Gly Asp Phe Ala Pro Val Phe Ala Arg Arg Leu
            260                 265                 270

Arg Ala Gly Asp Ser Val Leu Ala Pro Gly Gly Asp Ala Leu Arg Pro
        275                 280                 285

Ala Arg Val Ala Arg Val Ala Arg Glu Glu Ala Val Gly Val Phe Ala
    290                 295                 300

Pro Leu Thr Ala His Gly Thr Leu Leu Val Asn Asp Val Leu Ala Ser
305                 310                 315                 320

Cys Tyr Ala Val Leu Glu Ser His Gln Trp Ala His Arg Ala Phe Ala
                325                 330                 335

Pro Leu Arg Leu Leu His Ala Leu Gly Ala Leu Leu Pro Gly Gly Ala
            340                 345                 350

Val Gln Pro Thr Gly Met His Trp Tyr Ser Arg Leu Leu Tyr Arg Leu
        355                 360                 365

Ala Glu Glu Leu Leu Gly
    370
```

(2) INFORMATION FOR SEQ ID NO: 3:

(i) SEQUENCE CHARACTERISTICS:
        (A) LENGTH: 396 amino acids
        (B) TYPE: amino acid
        (C) STRANDEDNESS: single
        (D) TOPOLOGY: linear

```
    (ii) MOLECULE TYPE: protein (ix) FEATURE:
         (A) NAME/KEY: sig peptide
         (B) LOCATION: -22..-1
         (C) IDENTIFICATION METHOD: S
         (A) NAME/KEY: mat peptide
         (B) LOCATION: 1..176
         (C) IDENTIFICATION METHOD: S (xi) SEQUENCE DESCRIPTION: SEQ ID NO: 3:

Met Ala Leu Leu Thr Asn Leu Leu Pro Leu Cys Cys Leu Ala Leu Leu
            -20                 -15                 -10

Ala Leu Pro Ala Gln Ser Cys Gly Pro Gly Arg Gly Pro Val Gly Arg
     -5               1                5                      10

Arg Arg Tyr Ala Arg Lys Gln Leu Val Pro Leu Leu Tyr Lys Gln Phe
                 15                  20                  25

Val Pro Gly Val Pro Glu Arg Thr Leu Gly Ala Ser Gly Pro Ala Glu
             30                  35                  40

Gly Arg Val Ala Arg Gly Ser Glu Arg Phe Arg Asp Leu Val Pro Asn
             45                  50                  55

Tyr Asn Pro Asp Ile Ile Phe Lys Asp Glu Asn Ser Gly Ala Asp
     60                  65                  70

Arg Leu Met Thr Glu Arg Cys Lys Glu Arg Val Asn Ala Leu Ala Ile
75                   80                  85                  90

Ala Val Met Asn Met Trp Pro Gly Val Arg Leu Arg Val Thr Glu Gly
                 95                  100                 105

Trp Asp Glu Asp Gly His His Ala Gln Asp Ser Leu His Tyr Glu Gly
             110                 115                 120

Arg Ala Leu Asp Ile Thr Thr Ser Asp Arg Asp Arg Asn Lys Tyr Gly
             125                 130                 135

Leu Leu Ala Arg Leu Ala Val Glu Ala Gly Phe Asp Trp Val Tyr Tyr
    140                 145                 150

Glu Ser Arg Asn His Ile His Val Ser Val Lys Ala Asp Asn Ser Leu
155                 160                 165                 170

Ala Val Arg Ala Gly Gly Cys Phe Pro Gly Asn Ala Thr Val Arg Leu
                175                 180                 185

Trp Ser Gly Glu Arg Lys Gly Leu Arg Glu Leu His Arg Gly Asp Trp
            190                 195                 200

Val Leu Thr Ala Asp Ala Ser Gly Arg Val Val Pro Thr Pro Val Leu
            205                 210                 215

Leu Phe Leu Asp Arg Asp Leu Gln Arg Arg Ala Ser Phe Val Ala Val
    220                 225                 230

Glu Thr Glu Trp Pro Pro Arg Lys Leu Leu Thr Pro Trp His Leu
235                 240                 245                 250

Val Phe Ala Ala Arg Gly Pro Ala Pro Ala Pro Gly Asp Phe Ala Pro
                255                 260                 265

Val Phe Ala Arg Arg Leu Arg Ala Gly Asp Ser Val Leu Ala Pro Gly
                270                 275                 280

Gly Asp Ala Leu Arg Pro Ala Arg Val Ala Arg Val Ala Arg Glu Glu
            285                 290                 295

Ala Val Gly Val Phe Ala Pro Leu Thr Ala His Gly Thr Leu Leu Val
            300                 305                 310

Asn Asp Val Leu Ala Ser Cys Tyr Ala Val Leu Glu Ser His Gln Trp
315                 320                 325                 330

Ala His Arg Ala Phe Ala Pro Leu Arg Leu Leu His Ala Leu Gly Ala
```

```
                    335                 340                 345
Leu Leu Pro Gly Gly Ala Val Gln Pro Thr Gly Met His Trp Tyr Ser
        350                 355                 360

Arg Leu Leu Tyr Arg Leu Ala Glu Glu Leu Leu Gly
        365                 370
```

(2) INFORMATION FOR SEQ ID NO: 4:

(i) SEQUENCE CHARACTERISTICS:
        (A) LENGTH: 528 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat peptide
        (B) LOCATION: 1..528
        (C) IDENTIFICATION METHOD: S (xi) SEQUENCE DESCRIPTION: SEQ ID NO: 4:

```
TGC GGG CCG GGC CGG GGG CCG GTT GGC CGG CGC CGC TAT GCG CGC AAG      48
Cys Gly Pro Gly Arg Gly Pro Val Gly Arg Arg Arg Tyr Ala Arg Lys
 1               5                  10                  15

CAG CTC GTG CCG CTA CTC TAC AAG CAA TTT GTG CCC GGC GTG CCA GAG      96
Gln Leu Val Pro Leu Leu Tyr Lys Gln Phe Val Pro Gly Val Pro Glu
             20                  25                  30

CGG ACC CTG GGC GCC AGT GGG CCA GCG GAG GGG AGG GTG GCA AGG GGC     144
Arg Thr Leu Gly Ala Ser Gly Pro Ala Glu Gly Arg Val Ala Arg Gly
         35                  40                  45

TCC GAG CGC TTC CGG GAC CTC GTG CCC AAC TAC AAC CCC GAC ATC ATC     192
Ser Glu Arg Phe Arg Asp Leu Val Pro Asn Tyr Asn Pro Asp Ile Ile
     50                  55                  60

TTC AAG GAT GAG GAG AAC AGT GGA GCC GAC CGC CTG ATG ACC GAA CGT     240
Phe Lys Asp Glu Glu Asn Ser Gly Ala Asp Arg Leu Met Thr Glu Arg
 65                  70                  75                  80

TGT AAG GAA CGG GTG AAC GCT TTG GCC ATT GCC GTG ATG AAC ATG TGG     288
Cys Lys Glu Arg Val Asn Ala Leu Ala Ile Ala Val Met Asn Met Trp
                 85                  90                  95

CCC GGA GTG CGC CTA CGA GTG ACT GAG GGC TGG GAC GAG GAC GGC CAC     336
Pro Gly Val Arg Leu Arg Val Thr Glu Gly Trp Asp Glu Asp Gly His
            100                 105                 110

CAC GCT CAG GAT TCA CTC CAC TAC GAA GGC CGT GCT TTG GAC ATC ACT     384
His Ala Gln Asp Ser Leu His Tyr Glu Gly Arg Ala Leu Asp Ile Thr
        115                 120                 125

ACG TCT GAC CGC GAC CGC AAC AAG TAT GGG TTG CTG GCG CGC CTC GCA     432
Thr Ser Asp Arg Asp Arg Asn Lys Tyr Gly Leu Leu Ala Arg Leu Ala
    130                 135                 140

GTG GAA GCC GGC TTC GAC TGG GTC TAC TAC GAG TCC CGC AAC CAC ATC     480
Val Glu Ala Gly Phe Asp Trp Val Tyr Tyr Glu Ser Arg Asn His Ile
145                 150                 155                 160

CAC GTG TCG GTC AAA GCT GAT AAC TCA CTG GCG GTC CGG GCG GGC GGC     528
His Val Ser Val Lys Ala Asp Asn Ser Leu Ala Val Arg Ala Gly Gly
                165                 170                 175
```

(2) INFORMATION FOR SEQ ID NO: 5:

(i) SEQUENCE CHARACTERISTICS:
        (A) LENGTH: 1122 base pairs
        (B) TYPE: nucleic acid
        (C) STRANDEDNESS: double
        (D) TOPOLOGY: linear -continued

```
    (ii) MOLECULE TYPE: cDNA (ix) FEATURE:
         (A) NAME/KEY: mat peptide
         (B) LOCATION: 1..528
         (C) IDENTIFICATION METHOD: S (xi) SEQUENCE DESCRIPTION: SEQ ID NO: 5:

TGC GGG CCG GGC CGG GGG CCG GTT GGC CGG CGC CGC TAT GCG CGC AAG      48
Cys Gly Pro Gly Arg Gly Pro Val Gly Arg Arg Arg Tyr Ala Arg Lys
 1               5                  10                  15

CAG CTC GTG CCG CTA CTC TAC AAG CAA TTT GTG CCC GGC GTG CCA GAG      96
Gln Leu Val Pro Leu Leu Tyr Lys Gln Phe Val Pro Gly Val Pro Glu
                 20                  25                  30

CGG ACC CTG GGC GCC AGT GGG CCA GCG GAG GGG AGG GTG GCA AGG GGC     144
Arg Thr Leu Gly Ala Ser Gly Pro Ala Glu Gly Arg Val Ala Arg Gly
             35                  40                  45

TCC GAG CGC TTC CGG GAC CTC GTG CCC AAC TAC AAC CCC GAC ATC ATC     192
Ser Glu Arg Phe Arg Asp Leu Val Pro Asn Tyr Asn Pro Asp Ile Ile
         50                  55                  60

TTC AAG GAT GAG GAG AAC AGT GGA GCC GAC CGC CTG ATG ACC GAA CGT     240
Phe Lys Asp Glu Glu Asn Ser Gly Ala Asp Arg Leu Met Thr Glu Arg
 65                  70                  75                  80

TGT AAG GAA CGG GTG AAC GCT TTG GCC ATT GCC GTG ATG AAC ATG TGG     288
Cys Lys Glu Arg Val Asn Ala Leu Ala Ile Ala Val Met Asn Met Trp
                 85                  90                  95

CCC GGA GTG CGC CTA CGA GTG ACT GAG GGC TGG GAC GAG GAC GGC CAC     336
Pro Gly Val Arg Leu Arg Val Thr Glu Gly Trp Asp Glu Asp Gly His
                100                 105                 110

CAC GCT CAG GAT TCA CTC CAC TAC GAA GGC CGT GCT TTG GAC ATC ACT     384
His Ala Gln Asp Ser Leu His Tyr Glu Gly Arg Ala Leu Asp Ile Thr
            115                 120                 125

ACG TCT GAC CGC GAC CGC AAC AAG TAT GGG TTG CTG GCG CGC CTC GCA     432
Thr Ser Asp Arg Asp Arg Asn Lys Tyr Gly Leu Leu Ala Arg Leu Ala
130                 135                 140

GTG GAA GCC GGC TTC GAC TGG GTC TAC TAC GAG TCC CGC AAC CAC ATC     480
Val Glu Ala Gly Phe Asp Trp Val Tyr Tyr Glu Ser Arg Asn His Ile
145                 150                 155                 160

CAC GTG TCG GTC AAA GCT GAT AAC TCA CTG GCG GTC CGG GCG GGC GGC     528
His Val Ser Val Lys Ala Asp Asn Ser Leu Ala Val Arg Ala Gly Gly
                165                 170                 175

TGC TTT CCG GGA AAT GCA ACT GTG CGC CTG TGG AGC GGC GAG CGG AAA     576
Cys Phe Pro Gly Asn Ala Thr Val Arg Leu Trp Ser Gly Glu Arg Lys
                180                 185                 190

GGG CTG CGG GAA CTG CAC CGC GGA GAC TGG GTT TTG ACG GCC GAT GCG     624
Gly Leu Arg Glu Leu His Arg Gly Asp Trp Val Leu Thr Ala Asp Ala
            195                 200                 205

TCA GGC CGG GTG GTG CCC ACG CCG GTG CTG CTC TTC CTG GAC CGG GAC     672
Ser Gly Arg Val Val Pro Thr Pro Val Leu Leu Phe Leu Asp Arg Asp
210                 215                 220

TTG CAG CGC CGG GCT TCA TTT GTG GCT GTG GAG ACC GAG TGG CCT CCA     720
Leu Gln Arg Arg Ala Ser Phe Val Ala Val Glu Thr Glu Trp Pro Pro
225                 230                 235                 240

CGC AAA CTG TTG CTC ACG CCC TGG CAC CTG GTG TTT GCC GCT CGA GGG     768
Arg Lys Leu Leu Leu Thr Pro Trp His Leu Val Phe Ala Ala Arg Gly
                245                 250                 255

CCG GCG CCC GCG CCA GGC GAC TTT GCA CCG GTG TTC GCG CGC CGG CTA     816
Pro Ala Pro Ala Pro Gly Asp Phe Ala Pro Val Phe Ala Arg Arg Leu
                260                 265                 270

CGC GCT GGG GAC TCG GTG CTG GCG CCC GGC GGG GAT GCG CTT CGG CCA     864
Arg Ala Gly Asp Ser Val Leu Ala Pro Gly Gly Asp Ala Leu Arg Pro
```

-continued

```
              275                 280                 285
GCG CGC GTG GCC CGT GTG GCG CGG GAG GAA GCC GTG GGC GTG TTC GCG      912
Ala Arg Val Ala Arg Val Ala Arg Glu Glu Ala Val Gly Val Phe Ala
    290                 295                 300

CCG CTC ACC GCG CAC GGG ACG CTG CTG GTG AAC GAT GTC CTG GCC TCT      960
Pro Leu Thr Ala His Gly Thr Leu Leu Val Asn Asp Val Leu Ala Ser
305                 310                 315                 320

TGC TAC GCG GTT CTG GAG AGT CAC CAG TGG GCG CAC CGC GCT TTT GCC     1008
Cys Tyr Ala Val Leu Glu Ser His Gln Trp Ala His Arg Ala Phe Ala
                325                 330                 335

CCC TTG AGA CTG CTG CAC GCG CTA GGG GCG CTG CTC CCC GGC GGG GCC     1056
Pro Leu Arg Leu Leu His Ala Leu Gly Ala Leu Leu Pro Gly Gly Ala
            340                 345                 350

GTC CAG CCG ACT GGC ATG CAT TGG TAC TCT CGG CTC CTC TAC CGC TTA     1104
Val Gln Pro Thr Gly Met His Trp Tyr Ser Arg Leu Leu Tyr Arg Leu
        355                 360                 365

GCG GAG GAG CTA CTG GGC                                              1122
Ala Glu Glu Leu Leu Gly
    370
```

(2) INFORMATION FOR SEQ ID NO: 6:

(i) SEQUENCE CHARACTERISTICS:
        (A) LENGTH: 1188 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: sig peptide
        (B) LOCATION: 1..66
        (C) IDENTIFICATION METHOD: S
        (A) NAME/KEY: mat peptide
        (B) LOCATION: 67..594
        (C) IDENTIFICATION METHOD: S (xi) SEQUENCE DESCRIPTION: SEQ ID NO: 6:

```
ATG GCT CTC CTG ACC AAT CTA CTG CCC CTG TGC TGC TTG GCA CTT CTG       48
Met Ala Leu Leu Thr Asn Leu Leu Pro Leu Cys Cys Leu Ala Leu Leu
        -20                 -15                 -10

GCG CTG CCA GCC CAG AGC TGC GGG CCG GGC CGG GGG CCG GTT GGC CGG       96
Ala Leu Pro Ala Gln Ser Cys Gly Pro Gly Arg Gly Pro Val Gly Arg
    -5                   1                   5                  10

CGC CGC TAT GCG CGC AAG CAG CTC GTG CCG CTA CTC TAC AAG CAA TTT      144
Arg Arg Tyr Ala Arg Lys Gln Leu Val Pro Leu Leu Tyr Lys Gln Phe
                 15                  20                  25

GTG CCC GGC GTG CCA GAG CGG ACC CTG GGC GCC AGT GGG CCA GCG GAG      192
Val Pro Gly Val Pro Glu Arg Thr Leu Gly Ala Ser Gly Pro Ala Glu
             30                  35                  40

GGG AGG GTG GCA AGG GGC TCC GAG CGC TTC CGG GAC CTC GTG CCC AAC      240
Gly Arg Val Ala Arg Gly Ser Glu Arg Phe Arg Asp Leu Val Pro Asn
         45                  50                  55

TAC AAC CCC GAC ATC ATC TTC AAG GAT GAG GAG AAC AGT GGA GCC GAC      288
Tyr Asn Pro Asp Ile Ile Phe Lys Asp Glu Glu Asn Ser Gly Ala Asp
     60                  65                  70

CGC CTG ATG ACC GAA CGT TGT AAG GAA CGG GTG AAC GCT TTG GCC ATT      336
Arg Leu Met Thr Glu Arg Cys Lys Glu Arg Val Asn Ala Leu Ala Ile
 75                  80                  85                  90

GCC GTG ATG AAC ATG TGG CCC GGA GTG CGC CTA CGA GTG ACT GAG GGC      384
Ala Val Met Asn Met Trp Pro Gly Val Arg Leu Arg Val Thr Glu Gly
                 95                 100                 105
```

-continued

```
TGG GAC GAG GAC GGC CAC CAC GCT CAG GAT TCA CTC CAC TAC GAA GGC        432
Trp Asp Glu Asp Gly His His Ala Gln Asp Ser Leu His Tyr Glu Gly
            110                 115                 120

CGT GCT TTG GAC ATC ACT ACG TCT GAC CGC GAC CGC AAC AAG TAT GGG        480
Arg Ala Leu Asp Ile Thr Thr Ser Asp Arg Asp Arg Asn Lys Tyr Gly
            125                 130                 135

TTG CTG GCG CGC CTC GCA GTG GAA GCC GGC TTC GAC TGG GTC TAC TAC        528
Leu Leu Ala Arg Leu Ala Val Glu Ala Gly Phe Asp Trp Val Tyr Tyr
        140                 145                 150

GAG TCC CGC AAC CAC ATC CAC GTG TCG GTC AAA GCT GAT AAC TCA CTG        576
Glu Ser Arg Asn His Ile His Val Ser Val Lys Ala Asp Asn Ser Leu
155                 160                 165                 170

GCG GTC CGG GCG GGC GGC TGC TTT CCG GGA AAT GCA ACT GTG CGC CTG        624
Ala Val Arg Ala Gly Gly Cys Phe Pro Gly Asn Ala Thr Val Arg Leu
                175                 180                 185

TGG AGC GGC GAG CGG AAA GGG CTG CGG GAA CTG CAC CGC GGA GAC TGG        672
Trp Ser Gly Glu Arg Lys Gly Leu Arg Glu Leu His Arg Gly Asp Trp
                190                 195                 200

GTT TTG ACG GCC GAT GCG TCA GGC CGG GTG GTG CCC ACG CCG GTG CTG        720
Val Leu Thr Ala Asp Ala Ser Gly Arg Val Val Pro Thr Pro Val Leu
            205                 210                 215

CTC TTC CTG GAC CGG GAC TTG CAG CGC CGG GCT TCA TTT GTG GCT GTG        768
Leu Phe Leu Asp Arg Asp Leu Gln Arg Arg Ala Ser Phe Val Ala Val
        220                 225                 230

GAG ACC GAG TGG CCT CCA CGC AAA CTG TTG CTC ACG CCC TGG CAC CTG        816
Glu Thr Glu Trp Pro Pro Arg Lys Leu Leu Leu Thr Pro Trp His Leu
235                 240                 245                 250

GTG TTT GCC GCT CGA GGG CCG GCG CCC GCG CCA GGC GAC TTT GCA CCG        864
Val Phe Ala Ala Arg Gly Pro Ala Pro Ala Pro Gly Asp Phe Ala Pro
                255                 260                 265

GTG TTC GCG CGC CGG CTA CGC GCT GGG GAC TCG GTG CTG GCG CCC GGC        912
Val Phe Ala Arg Arg Leu Arg Ala Gly Asp Ser Val Leu Ala Pro Gly
                270                 275                 280

GGG GAT GCG CTT CGG CCA GCG CGC GTG GCC CGT GTG GCG CGG GAG GAA        960
Gly Asp Ala Leu Arg Pro Ala Arg Val Ala Arg Val Ala Arg Glu Glu
            285                 290                 295

GCC GTG GGC GTG TTC GCG CCG CTC ACC GCG CAC GGG ACG CTG CTG GTG       1008
Ala Val Gly Val Phe Ala Pro Leu Thr Ala His Gly Thr Leu Leu Val
300                 305                 310

AAC GAT GTC CTG GCC TCT TGC TAC GCG GTT CTG GAG AGT CAC CAG TGG       1056
Asn Asp Val Leu Ala Ser Cys Tyr Ala Val Leu Glu Ser His Gln Trp
315                 320                 325                 330

GCG CAC CGC GCT TTT GCC CCC TTG AGA CTG CTG CAC GCG CTA GGG GCG       1104
Ala His Arg Ala Phe Ala Pro Leu Arg Leu Leu His Ala Leu Gly Ala
                335                 340                 345

CTG CTC CCC GGC GGG GCC GTC CAG CCG ACT GGC ATG CAT TGG TAC TCT       1152
Leu Leu Pro Gly Gly Ala Val Gln Pro Thr Gly Met His Trp Tyr Ser
            350                 355                 360

CGG CTC CTC TAC CGC TTA GCG GAG GAG CTA CTG GGC                       1188
Arg Leu Leu Tyr Arg Leu Ala Glu Glu Leu Leu Gly
        365                 370
```

(2) INFORMATION FOR SEQ ID NO: 7:

(i) SEQUENCE CHARACTERISTICS:
      (A) LENGTH: 548 base pairs
      (B) TYPE: nucleic acid
      (C) STRANDEDNESS: double
      (D) TOPOLOGY: linear (ii) MOLECULE TYPE: cDNA (vi) ORIGINAL SOURCE:
    (A) ORGANISM: human
    (B) INDIVIDUAL ISOLATE: ARH-77, ATCC CRL-1621

(ix) FEATURE:
    (A) NAME/KEY: sig peptide
    (B) LOCATION: 1..18
    (C) IDENTIFICATION METHOD: S
    (A) NAME/KEY: mat peptide
    (B) LOCATION: 19..546
    (C) IDENTIFICATION METHOD: S (xi) SEQUENCE DESCRIPTION: SEQ ID NO: 7:

```
GCG CTG CCA GCC CAG AGC TGC GGG CCG GGC CGG GGG CCG GTT GGC CGG        48
Ala Leu Pro Ala Gln Ser Cys Gly Pro Gly Arg Gly Pro Val Gly Arg
    -5                   1               5                  10

CGC CGC TAT GCG CGC AAG CAG CTC GTG CCG CTA CTC TAC AAG CAA TTT        96
Arg Arg Tyr Ala Arg Lys Gln Leu Val Pro Leu Leu Tyr Lys Gln Phe
                15                  20                  25

GTG CCC GGC GTG CCA GAG CGG ACC CTG GGC GCC AGT GGG CCA GCG GAG       144
Val Pro Gly Val Pro Glu Arg Thr Leu Gly Ala Ser Gly Pro Ala Glu
            30                  35                  40

GGG AGG GTG GCA AGG GGC TCC GAG CGC TTC CGG GAC CTC GTG CCC AAC       192
Gly Arg Val Ala Arg Gly Ser Glu Arg Phe Arg Asp Leu Val Pro Asn
        45                  50                  55

TAC AAC CCC GAC ATC ATC TTC AAG GAT GAG GAG AAC AGT GGA GCC GAC       240
Tyr Asn Pro Asp Ile Ile Phe Lys Asp Glu Glu Asn Ser Gly Ala Asp
    60                  65                  70

CGC CTG ATG ACC GAA CGT TGT AAG GAA CGG GTG AAC GCT TTG GCC ATT       288
Arg Leu Met Thr Glu Arg Cys Lys Glu Arg Val Asn Ala Leu Ala Ile
75                  80                  85                  90

GCC GTG ATG AAC ATG TGG CCC GGA GTG CGC CTA CGA GTG ACT GAG GGC       336
Ala Val Met Asn Met Trp Pro Gly Val Arg Leu Arg Val Thr Glu Gly
                95                 100                 105

TGG GAC GAG GAC GGC CAC CAC GCT CAG GAT TCA CTC CAC TAC GAA GGC       384
Trp Asp Glu Asp Gly His His Ala Gln Asp Ser Leu His Tyr Glu Gly
            110                 115                 120

CGT GCT TTG GAC ATC ACT ACG TCT GAC CGC GAC CGC AAC AAG TAT GGG       432
Arg Ala Leu Asp Ile Thr Thr Ser Asp Arg Asp Arg Asn Lys Tyr Gly
        125                 130                 135

TTG CTG GCG CGC CTC GCA GTG GAA GCC GGC TTC GAC TGG GTC TAC TAC       480
Leu Leu Ala Arg Leu Ala Val Glu Ala Gly Phe Asp Trp Val Tyr Tyr
    140                 145                 150

GAG TCC CGC AAC CAC ATC CAC GTG TCG GTC AAA GCT GAT AAC TCA CTG       528
Glu Ser Arg Asn His Ile His Val Ser Val Lys Ala Asp Asn Ser Leu
155                 160                 165                 170

GCG GTC CGG GCG GGC GGC TG                                            548
Ala Val Arg Ala Gly Gly
                175
```

(2) INFORMATION FOR SEQ ID NO: 8:

(i) SEQUENCE CHARACTERISTICS:
        (A) LENGTH: 602 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (B) INDIVIDUAL ISOLATE: ARH-77, ATCC CRL-1621

(ix) FEATURE:
        (A) NAME/KEY: 5_UTR (B) LOCATION: 1..6
(C) IDENTIFICATION METHOD: S
(A) NAME/KEY: sig peptide
(B) LOCATION: 7..72
(C) IDENTIFICATION METHOD: S
(A) NAME/KEY: mat peptide
(B) LOCATION: 73..600
(C) IDENTIFICATION METHOD: S (xi) SEQUENCE DESCRIPTION: SEQ ID NO: 8:

```
GTATCC ATG GCT CTC CTG ACC AAT CTA CTG CCC CTG TGC TGC TTG GCA          48
       Met Ala Leu Leu Thr Asn Leu Leu Pro Leu Cys Cys Leu Ala
           -20             -15             -10

CTT CTG GCG CTG CCA GCC CAG AGC TGC GGG CCG GGC CGG GGG CCG GTT          96
Leu Leu Ala Leu Pro Ala Gln Ser Cys Gly Pro Gly Arg Gly Pro Val
            -5               1               5

GGC CGG CGC CGC TAT GCG CGC AAG CAG CTC GTG CCG CTA CTC TAC AAG         144
Gly Arg Arg Arg Tyr Ala Arg Lys Gln Leu Val Pro Leu Leu Tyr Lys
         10              15              20

CAA TTT GTG CCC GGC GTG CCA GAG CGG ACC CTG GGC GCC AGT GGG CCA         192
Gln Phe Val Pro Gly Val Pro Glu Arg Thr Leu Gly Ala Ser Gly Pro
 25              30              35              40

GCG GAG GGG AGG GTG GCA AGG GGC TCC GAG CGC TTC CGG GAC CTC GTG         240
Ala Glu Gly Arg Val Ala Arg Gly Ser Glu Arg Phe Arg Asp Leu Val
                 45              50              55

CCC AAC TAC AAC CCC GAC ATC ATC TTC AAG GAT GAG GAG AAC AGT GGA         288
Pro Asn Tyr Asn Pro Asp Ile Ile Phe Lys Asp Glu Glu Asn Ser Gly
             60              65              70

GCC GAC CGC CTG ATG ACC GAA CGT TGT AAG GAA CGG GTG AAC GCT TTG         336
Ala Asp Arg Leu Met Thr Glu Arg Cys Lys Glu Arg Val Asn Ala Leu
 75              80              85

GCC ATT GCC GTG ATG AAC ATG TGG CCC GGA GTG CGC CTA CGA GTG ACT         384
Ala Ile Ala Val Met Asn Met Trp Pro Gly Val Arg Leu Arg Val Thr
         90              95             100

GAG GGC TGG GAC GAG GAC GGC CAC CAC GCT CAG GAT TCA CTC CAC TAC         432
Glu Gly Trp Asp Glu Asp Gly His His Ala Gln Asp Ser Leu His Tyr
105             110             115             120

GAA GGC CGT GCT TTG GAC ATC ACT ACG TCT GAC CGC GAC CGC AAC AAG         480
Glu Gly Arg Ala Leu Asp Ile Thr Thr Ser Asp Arg Asp Arg Asn Lys
             125             130             135

TAT GGG TTG CTG GCG CGC CTC GCA GTG GAA GCC GGC TTC GAC TGG GTC         528
Tyr Gly Leu Leu Ala Arg Leu Ala Val Glu Ala Gly Phe Asp Trp Val
         140             145             150

TAC TAC GAG TCC CGC AAC CAC ATC CAC GTG TCG GTC AAA GCT GAT AAC         576
Tyr Tyr Glu Ser Arg Asn His Ile His Val Ser Val Lys Ala Asp Asn
 155             160             165

TCA CTG GCG GTC CGG GCG GGC GGC TG                                      602
Ser Leu Ala Val Arg Ala Gly Gly
170                 175
```

(2) INFORMATION FOR SEQ ID NO: 9:

(i) SEQUENCE CHARACTERISTICS:
       (A) LENGTH: 575 base pairs
       (B) TYPE: nucleic acid
       (C) STRANDEDNESS: double
       (D) TOPOLOGY: linear (ii) MOLECULE TYPE: cDNA (vi) ORIGINAL SOURCE:
        (A) ORGANISM: human
        (B) INDIVIDUAL ISOLATE: ARH-77, ATCC CRL-1621

(xi) SEQUENCE DESCRIPTION: SEQ ID NO: 9:

```
C GTG TCG GTC AAA GCT GAT AAC TCA CTG GCG GTC CGG GCG GGC GGC              46
  Val Ser Val Lys Ala Asp Asn Ser Leu Ala Val Arg Ala Gly Gly
  1               5                   10                  15

TGC TTT CCG GGA AAT GCA ACT GTG CGC CTG TGG AGC GGC GAG CGG AAA            94
Cys Phe Pro Gly Asn Ala Thr Val Arg Leu Trp Ser Gly Glu Arg Lys
                20                  25                  30

GGG CTG CGG GAA CTG CAC CGC GGA GAC TGG GTT TTG ACG GCC GAT GCG           142
Gly Leu Arg Glu Leu His Arg Gly Asp Trp Val Leu Thr Ala Asp Ala
                    35                  40                  45

TCA GGC CGG GTG GTG CCC ACG CCG GTG CTG CTC TTC CTG GAC CGG GAC           190
Ser Gly Arg Val Val Pro Thr Pro Val Leu Leu Phe Leu Asp Arg Asp
            50                  55                  60

TTG CAG CGC CGG GCT TCA TTT GTG GCT GTG GAG ACC GAG TGG CCT CCA           238
Leu Gln Arg Arg Ala Ser Phe Val Ala Val Glu Thr Glu Trp Pro Pro
65                  70                  75

CGC AAA CTG TTG CTC ACG CCC TGG CAC CTG GTG TTT GCC GCT CGA GGG           286
Arg Lys Leu Leu Leu Thr Pro Trp His Leu Val Phe Ala Ala Arg Gly
80                  85                  90                  95

CCG GCG CCC GCG CCA GGC GAC TTT GCA CCG GTG TTC GCG CGC CGG CTA           334
Pro Ala Pro Ala Pro Gly Asp Phe Ala Pro Val Phe Ala Arg Arg Leu
                100                 105                 110

CGC GCT GGG GAC TCG GTG CTG GCG CCC GGC GGG GAT GCG CTT CGG CCA           382
Arg Ala Gly Asp Ser Val Leu Ala Pro Gly Gly Asp Ala Leu Arg Pro
            115                 120                 125

GCG CGC GTG GCC CGT GTG GCG CGG GAG GAA GCC GTG GGC GTG TTC GCG           430
Ala Arg Val Ala Arg Val Ala Arg Glu Glu Ala Val Gly Val Phe Ala
            130                 135                 140

CCG CTC ACC GCG CAC GGG ACG CTG CTG GTG AAC GAT GTC CTG GCC TCT           478
Pro Leu Thr Ala His Gly Thr Leu Leu Val Asn Asp Val Leu Ala Ser
145                 150                 155

TGC TAC GCG GTT CTG GAG AGT CAC CAG TGG GCG CAC CGC GCT TTT GCC           526
Cys Tyr Ala Val Leu Glu Ser His Gln Trp Ala His Arg Ala Phe Ala
160                 165                 170                 175

CCC TTG AGA CTG CTG CAC GCG CTA GGG GCG CTG CTC CCC GGC GGG GCC           574
Pro Leu Arg Leu Leu His Ala Leu Gly Ala Leu Leu Pro Gly Gly Ala
                180                 185                 190

G                                                                         575

(2) INFORMATION FOR SEQ ID NO: 10:

(i) SEQUENCE CHARACTERISTICS:
        (A) LENGTH: 230 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (B) INDIVIDUAL ISOLATE: ARH-77, ATCC CRL-1621

(ix) FEATURE:
        (A) NAME/KEY: 3_UTR
        (B) LOCATION: 218..230
        (C) IDENTIFICATION METHOD: S (xi) SEQUENCE DESCRIPTION: SEQ ID NO: 10:

G TTC GCG CCG CTC ACC GCG CAC GGG ACG CTG CTG GTG AAC GAT GTC             46
  Phe Ala Pro Leu Thr Ala His Gly Thr Leu Leu Val Asn Asp Val
  1               5                   10                  15

CTG GCC TCT TGC TAC GCG GTT CTG GAG AGT CAC CAG TGG GCG CAC CGC            94
Leu Ala Ser Cys Tyr Ala Val Leu Glu Ser His Gln Trp Ala His Arg
```

```
                      20                  25                  30
GCT TTT GCC CCC TTG AGA CTG CTG CAC GCG CTA GGG GCG CTG CTC CCC         142
Ala Phe Ala Pro Leu Arg Leu Leu His Ala Leu Gly Ala Leu Leu Pro
                35                  40                  45

GGC GGG GCC GTC CAG CCG ACT GGC ATG CAT TGG TAC TCT CGG CTC CTC         190
Gly Gly Ala Val Gln Pro Thr Gly Met His Trp Tyr Ser Arg Leu Leu
        50                  55                  60

TAC CGC TTA GCG GAG GAG CTA CTG GGC TGAGCGTCCC AGG                      230
Tyr Arg Leu Ala Glu Glu Leu Leu Gly
        65                  70

(2) INFORMATION FOR SEQ ID NO: 11:

(i) SEQUENCE CHARACTERISTICS:
        (A) LENGTH: 522 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (B) INDIVIDUAL ISOLATE: A549, ATCC CRL-185

(ix) FEATURE:
        (A) NAME/KEY: mat peptide
        (B) LOCATION: 1..522
        (C) IDENTIFICATION METHOD: S (xi) SEQUENCE DESCRIPTION: SEQ ID NO: 11:

TGC GGA CCG GGC AGG GGG TTC GGG AAA AGG AGG CAC CCC AAA AAG CTG          48
Cys Gly Pro Gly Arg Gly Phe Gly Lys Arg Arg His Pro Lys Lys Leu
 1               5                  10                  15

ACC CCT TTA GCC TAC AAG CAG TTT ATC CCC AAT GTG GCC GAA AAG ACC          96
Thr Pro Leu Ala Tyr Lys Gln Phe Ile Pro Asn Val Ala Glu Lys Thr
                20                  25                  30

CTA GGC GCC AGC GGA AGG TAT GAA GGG AAG ATC TCC AGA AAC TCC GAG         144
Leu Gly Ala Ser Gly Arg Tyr Glu Gly Lys Ile Ser Arg Asn Ser Glu
        35                  40                  45

CGA TTT AAG GAA CTC ACC CCC AAT TAC AAC CCC GAC ATC ATA TTT AAG         192
Arg Phe Lys Glu Leu Thr Pro Asn Tyr Asn Pro Asp Ile Ile Phe Lys
 50                  55                  60

GAT GAA GAA AAC ACC GGA GCG GAC AGG CTG ATG ACT CAG AGG TGT AAG         240
Asp Glu Glu Asn Thr Gly Ala Asp Arg Leu Met Thr Gln Arg Cys Lys
 65                  70                  75                  80

GAC AAG TTG AAC GCT TTG GCC ATC TCG GTG ATG AAC CAG TGG CCA GGA         288
Asp Lys Leu Asn Ala Leu Ala Ile Ser Val Met Asn Gln Trp Pro Gly
                85                  90                  95

GTG AAA CTG CGG GTG ACC GAG GGC TGG GAC GAA GAT GGC CAC CAC TCA         336
Val Lys Leu Arg Val Thr Glu Gly Trp Asp Glu Asp Gly His His Ser
                100                 105                 110

GAG GAG TCT CTG CAC TAC GAG GGC CGC GCA GTG GAC ATC ACC ACG TCT         384
Glu Glu Ser Leu His Tyr Glu Gly Arg Ala Val Asp Ile Thr Thr Ser
        115                 120                 125

GAC CGC GAC CGC AGC AAG TAC GGC ATG CTG GCC CGC CTG GCG GTG GAG         432
Asp Arg Asp Arg Ser Lys Tyr Gly Met Leu Ala Arg Leu Ala Val Glu
 130                 135                 140

GCC GGC TTC GAC TGG GTG TAC TAC GAG TCC AAG GCA CAT ATC CAC TGC         480
Ala Gly Phe Asp Trp Val Tyr Tyr Glu Ser Lys Ala His Ile His Cys
145                 150                 155                 160

TCG GTG AAA GCA GAG AAC TCG GTG GCG GCC AAA TCG GGA GGC                 522
Ser Val Lys Ala Glu Asn Ser Val Ala Ala Lys Ser Gly Gly
                165                 170     174
```

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 12:

GCCAGGGTGT GAGCAACAGT                                                     20

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 13:

TGTGCTGCTT GGCACTCTTG                                                     20

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 14:

CCGTGGCATT TCCCGGAAAG                                                     20

(2) INFORMATION FOR SEQ ID NO: 15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 15:

GTATCCATGG CTCTCCTG                                                       18

(2) INFORMATION FOR SEQ ID NO: 16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 16:

GCCTCGAGGT ATCCATGGCT CTCCTG                                    26

(2) INFORMATION FOR SEQ ID NO: 17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 17:

GCGCGGCCGC TCAGCCGCCC GCCCGGAC                                 28

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 18:

CGTGTCGGTC AAAGCTGATA                                                   20

(2) INFORMATION FOR SEQ ID NO: 19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 19:

ATGCATTCCA GTCGGCTGGA                                                   20

(2) INFORMATION FOR SEQ ID NO: 20:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO: 20:

AAGGATCCGT CGACAAGCTT AATACGACGA ATTCTGGAGT TTTTTTTTTT TTTTTT          56

(2) INFORMATION FOR SEQ ID NO: 21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 21:

GGCTTCGACT GGGTCTACTA                                                   20

(2) INFORMATION FOR SEQ ID NO: 22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 22:

AAGGATCCGT CGACAAG                                                        17

(2) INFORMATION FOR SEQ ID NO: 23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 23:

ATGCGCTTCG GCCAGCG                                                        17

(2) INFORMATION FOR SEQ ID NO: 24:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 24:

GACAAGCTTA ATACGAC                                          17

(2) INFORMATION FOR SEQ ID NO: 25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 25:

GTTCGCGCCG CTCACCG                                          17

(2) INFORMATION FOR SEQ ID NO: 26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 26:

TACGACGAAT TCTGGAGT                                       18

(2) INFORMATION FOR SEQ ID NO: 27:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 27:

CCCGGGAATT CATTGCGGGC CGGGCCGGGG GCCG               34

(2) INFORMATION FOR SEQ ID NO: 28:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 28:

ACGATGAATT CTCAGCCGCC CGCCCGGACC GCCA               34

(2) INFORMATION FOR SEQ ID NO: 29:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 29:

Gly Ser Pro Gly Ile His
 1             5

(2) INFORMATION FOR SEQ ID NO: 30:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 30:

CCCGGGAATT CATTGCGGAC CGGGCAGGGG GTT    33

(2) INFORMATION FOR SEQ ID NO: 31:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO: 31:

ACGATGAATT CTCAGCCTCC CGATTTGGCC GC    32

HUMAN DESERT HEDGEHOG PROTEIN

This is a division of copending parent application Ser. No. 09/063,778, filed Apr. 22, 1998.

BACKGROUND OF THE INVENTION

1. Field of the Invention

This invention relates to a novel hedgehog protein, more particularly, a Desert hedgehog protein of human origin.

2. Description of the Prior Art

The hedgehog gene was originally identified by genetic techniques as a gene that plays an important role in normal morphogenesis during embryonic and larval development in the fruit fly *Drosophila melanogaster*, as described by C. Nusslein-Volhard et al., in Nature, Vol.287, pp.795–801 (1980). J. J. Lee et al. sequenced the gene and deduced the amino acid sequence of the hedgehog protein as the expression product in Cell, Vol.71, pp.33–50 (1992). Some homologues of the gene were later isolated from vertebrates including mammals (hereinafter, the homologues of species other than the fruit fly may also be called "hedgehog"). At present, it is known that vertebrate hedgehog genes, unlike that of the fruit fly, form a multigene family and would play different roles in normal morphogenesis.

For example, as described by Y. Echelard et al., in Cell, Vol.75, pp.1417–1430 (1993), there have been identified three types of the genes of mouse origin, designated "Sonic hedgehog", "Indian hedgehog", and "Desert hedgehog", which have different nucleotide sequences and express in different manners in living bodies. While in human, there have been found only two types of the genes designated "Sonic hedgehog" and "Indian hedgehog", as described by V. Marigo et al., in GENOMICS, Vol.28, pp.44–51 (1995), and their expression manners and functions of their expression products remain to be elucidated. Therefore from scientific and pharmaceutical viewpoints, in order to elucidate the process of exhibiting hereditary morphological abnormalities in humans and direct research their treatments and diagnoses, the establishment of a novel hedgehog gene and its expression product, i.e. a novel hedgehog protein, is now in great expectation demand.

SUMMARY OF THE INVENTION

In view of the foregoing, the first object of this invention is to provide a novel hedgehog protein of human origin.

The second object of this invention is to provide a DNA encoding the hedgehog protein.

The third object of this invention is to provide a monoclonal antibody recognizing the hedgehog protein.

The fourth object of this invention is to provide a process for producing the hedgehog protein.

The fifth object of this invention is to provide a method for detecting the hedgehog protein.

The present inventors energetically and extensively screened for human cell lines which express a novel hedgehog gene capable of attaining the above objects by using RT-PCR techniques, where RNAs obtained from various established human cell lines were used as templates, while as primers various oligonucleotides were chemically synthesized based on the nucleotide sequence of mouse Desert hedgehog gene registered in "GenBank®", a nucleic acid database by National Institute of Health, USA, under the accession number "X76292". These screenings resulted in finding that some human cell lines including ARH-77 cell, ATCC CRL-1621, a cell line derived from plasma cell of a leukemia patient, expressed a specific gene in an elevated level checked with the above RT-PCRs. Further energetic studies confirmed that the human gene was a novel gene, which contained no known nucleotide sequences. Comparison with other genes revealed that the human gene has a relatively high homology to mouse Desert hedgehog gene. These findings led to the conclusion that the gene is a novel type of Desert hedgehog gene of human origin. A DNA obtained from the gene thus sequenced was introduced into *Escherichia coli* using an autonomously replicable vector, attaining satisfactory DNA expression and production of human Desert hedgehog protein.

Furthermore, the present inventors prepared known human Sonic hedgehog protein by using conventional recombinant DNA techniques and prepared monoclonal antibodies recognizing the protein. It was found that some of the monoclonal antibodies unexpectedly recognized well not only human Sonic hedgehog protein but also human Desert hedgehog protein. This invention was established based on these findings.

More particularly, the first object of this invention is attained by a Desert hedgehog protein of human origin.

The second object of this invention is attained by a DNA which encodes the hedgehog protein.

The third object of this invention is attained by a monoclonal antibody which recognizes the hedgehog protein.

The forth object of this invention is attained by a process for preparing a hedgehog protein which comprises the steps of allowing to express a DNA encoding the hedgehog protein and collecting the generated hedgehog protein.

The fifth object of this invention is attained by a method for detecting the hedgehog protein using a monoclonal antibody which recognizes the hedgehog protein.

BRIEF DESCRIPTION OF THE ACCOMPANYING DRAWINGS

Figure 1:
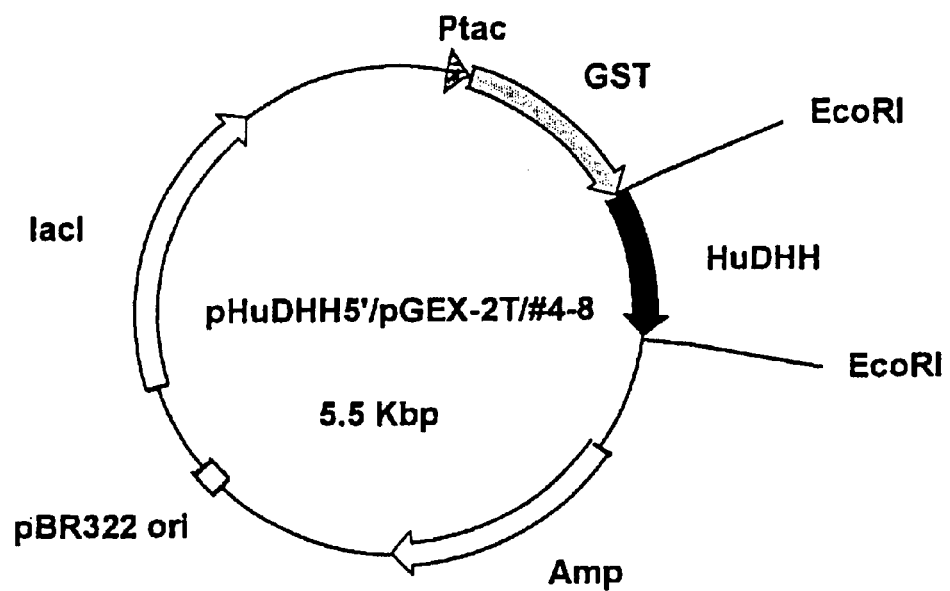
FIG. 1 is the restriction map of the recombinant DNA of this invention "pHuDHH/pGEX-2T/#4-8".

In FIG. 1, the symbol "HuDHH" indicates a DNA encoding the hedgehog protein of this invention; the symbol "Amp", an ampicillin-resistant gene; the symbol "pBR322ori", a replication origin exerting in *Escherichia coli*; the symbol "GST", a structural gene of glutathione S-transferase; and the symbol "Ptac", a Tac promotor.

DETAILED DESCRIPTION OF THE INVENTION

This invention relates to a novel hedgehog protein, more particularly, a Desert hedgehog protein of human origin. The present hedgehog protein contains a part or the whole of the amino acid sequence of SEQ ID NO:1, which may bear a homology, usually about 80%, to mouse Desert hedgehog protein at amino acid sequence level. Examples of the present hedgehog protein are a mature form of human Desert hedgehog protein that contains the amino acid sequence of SEQ ID NO:1 and a precursor form of human Desert hedgehog protein that has the amino acid sequence of SEQ ID NO:2 or 3, which contains the amino acid sequence of SEQ ID NO:1. The present hedgehog protein further includes other types of proteins with amino acid sequences as illustrated above where where one or more amino acids are deleted or replaced with other ones, one or more amino acids are added, or saccharide chains are linked, so far as they contain the amino acid sequence as mentioned above. The present hedgehog protein shall not be restricted to those obtained from specific sources and by specific preparation methods, threrefor it include natural proteins obtained from cultures of established cell lines, recombinant proteins obtained by recombinant DNA techniques, and synthetic polypeptides obtained by way of peptide synthesis.

The DNA of this invention includes any DNAs which encode such hedgehog protein, regardless of their sources or origins. Thus the DNA of this invention include those from natural sources as well as those artificially modified or chemically synthesized, as far as they encode the hedgehog protein of this invention. Generally in this field, in case of artificially expressing DNAs which encode proteins, one may replace one or more nucleotides in the DNAs with different nucleotides and/or link appropriate nucleotide sequences thereto with the purpose of improving their expression efficiency and/or the physiological and physicochemical properties of the protein. Such modification are feasible in the DNA of this invention. More particularly, one can link, for example, to the 5'- and/or 3'-termini of the DNA as described above, recognition sites for appropriate restriction enzymes, initiation codons, termination codons, promoters and/or enhancers, as far as the final protein products do retain prescribed properties. Thus, the wording "DNA" as referred to in this invention shall mean, in addition to those which encode the above-mentioned proteins, those which are complementary thereto, and those where one or more nucleotides have been replaced with different nucleotides while conserving the encoding amino acid sequence.

Such a DNA can be obtained from natural by screening of human cells, for example, mammalian cells including epithelial cells, endothelial cells, interstitial cells, chondrocytes, monocytes, granulocytes, lymphocytes, neurocytes, and established cell lines from them of human origin, based on a hybridization with a DNA as a probe which encodes at least a part of the amino acid sequence of human Desert hedgehog protein of this invention, for example, the amino acid sequence of SEQ ID NO:1. Such screening can be achieved with conventional methods commonly used in this field such as PCR, RT-PCR, screening cDNA libraries, screening genomic libraries and/or modified methods thereof. Examples of preferred cells are established cell lines including ARH-77 cell, ATCC CRL-1621, K-562 cell, ATCC CCL-243, and KU-812 cell, an cell line reported by K. Kishi, in *Leukemia Research*, Vol.9, pp.381–390 (1985), and bone mallow cells. The DNA of this invention thus obtained usually contains a part or the whole of the nucleotide sequence of SEQ ID NO:4. For example, from ARH-77 cell, ATCC CRL-1621, a DNA encoding a mature form of human Desert hedgehog protein that contains the nucleotide sequence of SEQ ID NO:4 or a DNA encoding a precursor form of human Desert hedgehog protein that has the nucleotide sequence of SEQ ID NO:5 or 6, which contains the nucleotide sequence of SEQ ID NO:4, can be obtained. The present DNA can also be obtained by conventional chemical synthesis. The DNA of this invention, once obtained in any manner, can be easily amplified to desired level by methods of PCR or those using autonomously replicable vectors.

The DNA of this invention includes those in the forms of recombinant DNAs where the DNA, encoding the present hedgehog protein, is inserted into autonomously replicable vectors. The recombinant DNAs can be relatively-easily obtained by using conventional recombinant DNA techniques, once the desired DNA is obtained. Examples of the vectors feasible in this invention are plasmid vectors including pGEX-2T, pGEX-4T-1, pKK223-3, pcDNAI/Amp, BCMGSNeo, pcDL-SRα, pKY4, pCDM8, pCEV4, and pME18S. The autonomously replicable vectors usually comprise nucleotide sequences suitable for the DNA expression in respective hosts, for example, promoters, enhancers, replication origins, terminators for transcription, splicing sequences, and/or sequences for selection markers. As the promotor, using a heat shock protein promotor or the interferon-α promotor disclosed in Japanese Patent Kokai No.163,368/95 by the same applicant makes it possible to regulate the present DNA expression in the transformants by external stimuli.

To insert the DNA of this invention, conventional methods comonly used in this field can be used. More particularly, a gene containing the DNA of this invention and an autonomously replicable vector are first cleaved with restriction enzymes and/or ultrasonication, then the resulting DNA and vector fragments are ligated. Ligation of the DNA and vector fragments become much easier when the genes and vectors are digested with restriction enzymes specific to particular nucleotides, for example, AccI, BamHI, BstXI, EcoRI, HindIII, NotI, PstI, SacI, SalI, SmaI, SpeI, XbaI and XhoI. To ligate the DNA and vector fragments, they can be first annealed, if necessary, and then exposed to DNA ligase in vivo or in vitro. The recombinant DNAs thus obtained are unlimitedly replicable in hosts of microbe and animal origins.

The DNA of this invention further includes those in the forms where the DNA, encoding the above-mentioned hedgehog protein, is introduced into desired hosts. The DNA in such forms can be obtained without considerable difficulty by introducing the recombinant DNA of this invention to desired hosts. For the hosts, cells of microbe, animal or plant origin conventionally used in this field can be arbitrarily used. The use of the hosts of microbe origin has a merit of a higher productivity of the protein per culture. The hosts of animal origin including mammals' has a merit that the protein produced is substantially or nearly equivalent to physicochemical properties of the protein obtained as a natural product. For the microbe hosts, for example, *Escherichia coli, Bacillus* species, *Streptomyces* species, and yeasts can be arbitrarily used. Examples of the mammalian hosts are epithelial cell, interstitial cell and hemopoietic cell of human, monkey, mouse and hamster origins including 3T3-Swiss albino cell, ATCC CCL-92, C127I cell, ATCC CRL-1616, CHO-K1 cell, ATCC CCL-61, CV-1 cell, ATCC CCL-70, COS-1 cell, ATCC CRL-1650, HeLa cell, ATCC CCL-2, MOP-8 cell, ATCC CRL1709, and their mutant strains. To introduce the DNA of this invention into such hosts, one can employ conventional methods, for example, DEAE-dextran method, calcium phosphate transfection method, electroporation method, lipofection method, microinjection method, and viral infection method using retrovirus, adenovirus, herpesvirus and vaccinia virus. To select clones capable of producing the protein among the resulting transformants, the transformants are cultivated in culture media, followed by selection of clones where production of the protein was observed. The above-mentioned recombinant DNA techniques are detailed in, for example, *Jikken-Igaku-Bessatsu, Saibo-Kogaku Handbook* (The handbook for the cell engineering), edited by Toshio KUROKI, Masaru TANIGUCHI and Mitsuo OSHIMURA, published by Yodosha. Co., Ltd., Tokyo, Japan (1992), and

*Jikken-Igaku-Bessatsu, Biomanual Series 3, Idenshi-Cloning-Jikken-Ho* (The experimental methods for the gene cloning), edited by Takashi YOKOTA and Kenichi ARAI, published by Yodosha Co., Ltd., Tokyo, Japan (1993).

In this field, once a desired DNA is obtained as described above, then the DNA can be conventionally introduced into animals or plants to establish "transgenic animals" or "transgenic plants". The transgenic animals and plants introduced with the DNA of this invention are also included by the DNA of this invention. The following outlines a procedure for establishing transgenic animals. At first, the DNA of this invention can be introduced into oosperms or embryonic stem cells by using microinjection method, electroporation method or infections with recombinant virus containing the DNA of this invention. Subsequently, thus-obtained cells introduced with the present DNA can be grafted into uterine tubes or uteruses of para-pregnant female animals. Thereafter, from the newborns delivered spontaneously or by caesarean, the transgenic animals introduced with the present DNA can be selected by hybridization method, PCR method, etc. The DNA to be introduced for the establishment of transgenic animals can comprise not only a nucleotide sequence for the present hedgehog protein but also other sequences for promotors or enhancers suitable for regulating the gene expression in desired tissue- and/or stimulation-specific manner and/or further other sequences for signal peptides. Thus, the transgenic animals introduced with the DNA of this invention can be obtained. Techniques for transgenic animals are detailed in a publication such as *Jikken-Igaku-Bessatsu, Shin-Idenshikogaku-Handbook* (The Handbook for Genetic Engineering), edited by Masami MURAMATSU, Hiroto OKAYAMA, and Tadashi Yamamoto, published by Yodosha Co., Ltd., Tokyo, Japan (1996), pp.269–283.

The present hedgehog protein can be prepared by the process of this invention comprising the steps of allowing to express a DNA encoding the hedgehog protein and collecting the generated hedgehog protein. The DNA expression step can include a step of culturing the above-mentioned transformants introduced with the DNA of this invention, encoding the hedgehog protein. The media used to culture the transformant can be selected from conventional ones depending on the types of the transformants to be used, and they are usually composed of, as a base, a bufferized water and, as additives, inorganic ions such as sodium ion, potassium ion, calcium ion, phosphoric ion and chloric ion; microelements, carbon sources, nitrogen sources, amino acids and vitamins which meet to the metabolism of particular hosts; and, optionally, sera, hormones, cell growth factors and cell adhesion factors. Examples of the carbon sources are saccharides including glucose, fructose, sucrose, starches, and partial hydrolyzates of starches, and examples of the nitrogen sources are nitrogen-containing inorganic and organic substances including ammonia, ammonium ions, urea, nitric ions, peptone, and yeast extracts.

Examples of the culture media are as follows: those for microbe hosts such as L broth medium, T broth medium, TY broth medium, nutrient broth medium, YM broth medium, and potato-dextrose medium; and those for animal hosts such as 199 medium, DMEM medium, Ham's F12 medium, IMDM medium, MCDB104 medium, MCDB153 medium, MEM medium, RD medium, RITC80-7 medium, RPMI-1630 medium, RPMI-1640 medium, WAJC404 medium. To the culture media, the transformant can be inoculated in a cell density of $1 \times 10^4$–$1 \times 10^7$ cells/ml, preferably, $1 \times 10^5$–$1 \times 10^6$ cells/ml, and cultured under conditions suitable for the hosts, if necessary, while the culture media are replaced with fresh preparations. In particular, when using the hosts of microbe origins, the culture can be carried out at a temperature of 25–65° C. and a pH of 5-8 under aerobic conditions such as agitation-aeration for 1–10 days. When using the hosts of animal origins, the culture can be carried out at a temperature of about 37° C. for one day to one week, preferably, two to four days by suspension- or monolayer culture. Thus cultures containing the present hedgehog protein are obtained. The content of the present hedgehog protein in the cultures, which may differ depending on the types of the transformants and culture conditions, is usually one microgram to 100 mg per liter.

Furthermore, in the process for preparing the hedgehog protein of this invention, the DNA expression step can include a step of culturing cells which express the hedgehog protein, for example, established human cell lines ARH-77 cell, ATCC CRL-1621, K-562 cell, ATCC CCL-243, and KU-812 cell, described by K. Kishi et al., in *Leukemia Research*, Vol.9, pp.381–390 (1985). By culturing such cells in culture media suitable for respective cells, for example, 199 medium, DMEM medium, Ham's F12 medium, IMDM medium, MCDB104 medium, MCDB153 medium, MEM medium, RD medium, RITC80-7 medium, RPMI-1630 medium, RPMI-1640 medium, and WAJC404 medium similarly as in culturing of the trasnformants using animal host cells as mentioned above, then the culture containing the present hedgehog protein can be obtained. The content of the present protein in the cultures, which may differ depending on the types of the cells and culture conditions, is usually one nanogram to one milligram per liter.

The culture products obtained in these manners can be first subjected to ultrasonication, cell-lytic enzyme and/or detergent to disrupt cells, if necessary, the present hedgehog protein can be separated from the cells or cell debris by filtration and centrifugation, followed by purification. In the purification, the culture products which have been separated from cells or cell debris can be subjected to conventional methods used to purify biologically-active proteins, for example, salting-out, dialysis, filtration, concentration, fractional precipitation, ion-exchange chromatography, gel filtration chromatography, adsorption chromatography, isoelectric focusing chromatography, hydrophobic chromatography, reversed phase chromatography, affinity chromatography, gel electrophoresis and isoelectric focusing gel electrophoresis which are used in combination, if necessary. The purified preparation of the present hedgehog protein can be concentrated and lyophilized into a liquid or solid form to meet to its final use. Immunoaffinity chromatographies using the monoclonal antibody described below do yield a high-purity preparation of the hedgehog protein with minimized costs and labors.

In the process of this invention for producing the hedgehog protein, the DNA expression step can also include a step of feeding or planting the transgenic animals or plants obtained by introducing the DNA which encodes the present hedgehog protein to animals other than humans or plants. After feeding or planting occasionally with desired stimuli, desired tissues, organs, bloods, milks, and/or body fluids of the resultants can be collected and subjected to the steps for purifying the hedgehog protein of this invention as mentioned above to obtain the present protein.

The monoclonal antibody of this invention includes the monoclonal antibodies in general which recognize the hedgehog protein of this invention, independently of its origins, sources, and classes. The monoclonal antibody of this invention can be obtained by using as an antigen the present hedgehog protein, other conventional hedgehog protein or antigenic fragment thereof, and more particularly, by preparing hybridoma cells of derived from an infinitely-proliferative of a mammal and an antibody-producing cell of a mammal that has been immunized with such an antigen, selecting clones of hybridoma capable of producing the monoclonal antibody of this invention, and culturing the clones in vitro or in vivo.

Proteins feasible as the antigens can be obtained through culturing of transformants introduced with a DNA encoding at least a partial amino acid sequence of SEQ ID NO:1, and the proteins are usually used after completely or partially purified. The antigenic fragments can be obtained by chemically or enzymatically digesting the completely or partially purified proteins or by chemical synthesis based on the amino acid sequence of SEQ ID NO:1, 2, or 3. Alternatively, the antigens can be obtained by using these techniques based on known hedgehog genes or proteins. Human Sonic hedgehog is useful as such known hedgehog.

Immunization of animals is conducted in conventional manner. For example, the antigens as described above can be injected alone or together with appropriate adjuvants into mammals through an intravenous, intradermal, subcutaneous or intraperitoneal route, and then the mammals can be fed for a prescribed time period. There is no limitation in types of the mammals, therefore any mammals can be used regardless of their types, sizes and genders, as far as one can obtain desired antigen-producing cells therefrom. Rodents such as rats, mice and hamsters are generally used, and among these the most desirable mammal can be chosen in respect to their compatibility with the infinitely-proliferative cells mentioned below. The dose of the antigen is generally set to about five to 500 μg/animal in total, which can be divided into two to five times inoculations with intervals of about one to two weeks, depending on the types and sizes of the mammals to be used. Three to five days after the final inoculation, the spleens are extracted and dispersed to obtain splenocytes as antibody-producing cells.

The antibody-producing cells obtained in this way can be then fused with infinitely-proliferative cells of mammalian origin to obtain cell-fusion products containing the objective hybridoma. Examples of the infinitely-proliferative cells usually used in this invention are cell lines of mouse myeloma origin such as P3/NSI/1-Ag4-1 cell, ATCC TIB-18; P3X63Ag8 cell, ATCC TIB-9; SP2/O-Ag14 cell, ATCC CRL-1581; and mutant strains thereof. The cell-fusion can be conducted in conventional manner using an electric pulse or a cell-fusion accelerator such as polyethylene glycol and Sendai virus. For example, the antibody-producing cells and the infinitely-proliferative cells of mammalian origin are co-suspended to give a ratio of about 1:1 to 1:10 in a cell fusion medium with such an accelerator and incubated at about 30 to 40° C. for about one to five minutes. Although conventional media such as minimum essential medium (MEM), RPMI-1640 medium, and Iscove's modified Dulbecco's medium are feasible as cell fusion media, it is desirable to remove the serum in media, such as bovine serum, prior to their use.

To select the objective hybridomas, the cell-fusion products thus obtained can be transferred to an appropriate selection medium, such as HAT medium, and the hybridomas are cultured at about 30 to 40° C. for 3 days to 3 weeks till the cells other than the hybridomas die. The hybridoma cells can be then cultured in usual manner and antibodies secreted in the medium can be tested for reactivity with the hedgehog protein of this invention. Such tests can be conducted in conventional manner directed to detection of antibodies in general, for example, enzyme-immunoassays, radioimmunoassays and bioassays, which are detailed in *Tan-Clone-Kotai-Jikken-Manual* (Experimental Manual for Monoclonal Antibody), edited by Sakuji TOYAMA and Tamie ANDO, published by Kodansha Scientific, Ltd., Tokyo, Japan (1991), pp.105–152. The hybridomas which recognize the present protein can be immediately cloned by the limiting dilution method, thus obtaining the singly cloned hybridomas according to this invention.

The monoclonal antibody of this invention can be obtained by culturing such hybridomas in vitro or in vivo. In culturing the hybridomas, conventional methods for culturing mammalian cells can be employed. More particularly, the monoclonal antibody can be collected from culture products in case of culturing in vitro in nutrient media, while the monoclonal antibody can be collected from the ascites and/or bloods of the animals in case of transplanting in non-human warm-blooded animals or culturing in vivo. To collect the monoclonal antibody from cultures, ascites and blood, conventional methods for purifying antibodies can be arbitrarily used. Particular methods are, for example, salting-out, dialysis, filtration, concentration, fractional precipitation, ion-exchange chromatography, gel filtration chromatography, adsorption chromatography, isoelectric focusing chromatography, hydrophobic chromatography, reversed phase chromatography, affinity chromatography, gel electrophoresis and isoelectric focusing gel electrophoresis which can be used in combination if necessary. The purified preparations of the monoclonal antibody can then be concentrated and dehydrated into liquids or solids to meet to their final use.

The monoclonal antibody of this invention is particularly useful in immunoaffinity chromatographies for purifying the present hedgehog protein. The method for purification usually comprises the steps of allowing the monoclonal antibody to contact with a mixture of the present protein and contaminants to adsorb the present hedgehog protein on the monoclonal antibody, and desorbing the protein from the antibody; these steps are usually conducted in aqueous systems. The monoclonal antibody of this invention can be used after being immobilized on gels of water-insoluble carriers and packed into columns. For example., the cultures of the transformants or their partially purified preparations are charged to such columns and run, resulting in that the hedgehog protein is substantially-selectively adsorbed by the monoclonal antibody on such carriers. The adsorbed protein can be easily desorbed by altering the hydrogen-ion concentration around the monoclonal antibody. For example, the desorption for eluting the protein is usually conducted under acidic conditions, preferably, pH 2-3 when using the monoclonal antibody belonging to immunoglobulin G (IgG), or alkaline conditions, preferably, pH 10-11 when using the monoclonal antibody belonging to immunoglobulin M (IgM). The present method can yield a high-purity preparation of the present hedgehog protein with minimized costs and labors.

The monoclonal antibody of this invention additionally has wide uses required to detect the present hedgehog protein. The use of the monoclonal antibody in label-immunoassays such as radioimmunoassays, enzyme-immunoassays, and fluorescent-immunoassays can make more rapidly and accurately detect the present hedgehog protein in samples qualitatively or quantitatively. In these immunoassays, the present monoclonal antibody can be used after being labelled with radioactive substances, enzymes, and/or fluorescent substances. The label-immunoassays have a merit that they can analyze more numerous samples at a time and more accurately than bioassays. Thus the detection method of this invention is significantly useful for quality controls of the present protein during processes of the production or the products, as well as for diagnoses of diseases by detecting the present hedgehog protein. This invention does not basically relate to the techniques for labelling monoclonal antibodies or label-assays, so that it does not describe them in detail. Such techniques are detailed in a publication such as *Enzyme immunoassay*, edited by P. Tijssen, translated by Eiji ISHIKAWA, published by Tokyo-Kagaku-Dojin, Tokyo, Japan (1989), pp.196–348.

The DNA of this invention, which encodes the present hedgehog protein, is also useful in "gene therapies". Particularly, in usual gene therapies, the DNA of this invention can be first inserted into a vector derived from virus such as retrovirus, adenovirus or adeno-associated virus, alternatively, embedded in either cationic- or membrane fusible-liposomes. Subsequently, the inserted or embedded DNA can be directly injected into patients with the hedgehog protein susceptive diseases, alternatively, introduced in vitro into lymphocytes, which have been collected from the patients, and self-implanted to the patients. Thus, the DNA of this invention exhibits a remarkable efficacy in gene therapies for diseases being susceptive to human Desert hedgehog protein. General procedures for gene therapies are detailed in *Jikken-Igaku-Bessatsu, Biomanual UP Series, Idenshichiryo-no-Kisogijutsu* (Basic techniques for the gene therapy), edited by Takashi SHIMADA, Izumi SAITO, and Keiya OZAWA, published by Yodosha Co., Ltd., Tokyo, Japan (1996).

The following Examples describe in detail the way of practicing this invention. The hedgehog protein of this invention, the DNA encoding the hedgehog protein, and the process for producing the hedgehog protein are explained by Examples 1 to 3, the monoclonal antibody of this invention and process for preparing the antibody are explained by Example 4, and the method for detecting the hedgehog protein using the monoclonal antibody of this invention is explained by Examples 5 and 6. The following Examples can be diversified by the technical level in this field. In view of this, this invention should not be restricted to the Examples:

Example 1

Preparation of DNA

Example 1-1(a)

Preparation of Total RNA

ARH-77 cells, ATCC CRL-1621, an established cell line derived from human plasma cell leukemia, were suspended in RPMI1640 medium supplemented with 10%(v/v) fetal bovine serum and proliferated in usual manner at 37° C. in a 5%(v/v) $CO_2$ incubator while scaling up the culture. After the cell density reached a desired level, the cells were collected. The cells were suspended in micro-centrifugal tubes with phosphate-beffered saline (hereinafter, abbreviated as "PBS") and centrifuged, and the supernatants were discarded; these treatments were repeated three times. Then the cells were placed in fresh micro-centrifugal tubes in an amount of $5 \times 10^6$ cells/tube, and "ULTRASPEC™ RNA", a total RNA isolation reagent commercialized by BIOTECX Laboratories, Inc., Houston, Tex., USA, was added to the tubes in a volume of 1.0 ml/tube before the cells were suspended. The suspensions were allowed to stand in ice-chilling conditions for 5 minutes, mixed with 1.2 ml/tube of a mixture of chloroform/"ULTRASPEC™ RNA" (⅕ by volume), shaken for 15 seconds, and allowed to stand in ice-chilling conditions for 5 minutes. Upper phase in the tubes formed by centrifugation was collected, mixed with the equal volume of 2-propanol, and allowed to stand in ice-chilling conditions for five minutes. The mixture was centrifuged, and the supernatant was discarded. The formed precipitate was washed twice with 75%(v/v) aqueous ethanol, dried up in vacuo, and dissolved in sterile distilled water, resulting in obtaining an aqueous solution containing total RNAs of ARH-77 cells. A small portion of the solution was examined for the absorbance at 260 nm to calculate an RNA content.

Example 1-1(b)

Preparation of First Strand cDNA

Based on the nucleotide sequence of a mouse Desert hedgehog gene registered in "GenBank® ", a nucleic acid database by National Institute of Health, USA, under the accession number "X76292", an oligonucleotide with the nucleotide sequence of 5'-GCCAGGGTGTGAGCAACAGT-3' (SEQ ID NO:12) was prepared in usual manner. In a micro-reaction tube, 2.5 pmol of the oligonucleotide and one microgram of total RNAs prepared by the method in Example 1-1(a) were placed, and sterile distilled water was added to the mixture to give a final volume of 15.5 μl. After the tube was allowed to stand at 70° C. for ten minutes and under ice-chilling conditions for one minute, to the tube 2.5 μl of 10×PCR buffer, 2.5 μl of 25 mM MgCl2, 1.0 μl of 10 mM dNTP mix, and 2.5 μl of 0.1 M DTT were added in this order. The tube was allowed to stand at 42° C. for one minute. First strand cDNAs was synthesized by adding to the tube one microliter of "SUPERSCRIPT II RT", a reagent of reverse transcriptase commercialized by GIBCO BRL, Life Technologies, Inc., Rockville, Md., USA, and incubating the tube at 42° C. for 50 minutes. After the mixture was heated to terminate the reaction at 70° C. for 15 minutes and cooled to 37° C., the RNAs were degraded by incubating with admixed one microliter of RNase at 37° C. for 30 minutes. Thereafter, from the reaction mixture, an aqueous solution containing purified first strand cDNAs in a volume of 50 μl was obtained by mixing with 120 μl of 6 M NaI and treating with "GlassMAX™", a DNA isolation matrix commercialized by GIBCO BRL, Life Technologies, Inc., Rockville, Md., USA, in accordance with the accompanying instructions.

Example 1-1 (c)

Preparation of DNA Fragment Encoding the Hedgehog Protein and Recombinant DNA

Ten-microliter portion of a solution of first strand cDNAs, obtained by the method in Example 1-1 (b), was sampled in a micro-reaction tube and manipulated with "5' RACE SYSTEM, VERSION 2.0", a kit for a modified PCR method of 5' RACE, commercialized by GIBCO BRL Life Technologies, Inc., Rockville, Md., USA, in accordance with the accompanying instructions to add a poly(C)-tail to each of the 5'-termini of the cDNAs and amplify DNA fragments for the 5'-terminal regions. The sense primer used was "anchor primer" in the kit, and the antisense primer used was the oligonucleotide in Example 1-1(b). The thermal controls were as follows: an incubation at 94° C. for one minute; 35 cycles of incubations at 94° C. for one minute, at 55° C. for one minute, and at 72° C. for one minute; and an incubation at 72° C. for 10 minutes. The reaction volume was set to 50 μl.

A DNA fragment which encodes a Desert hedgehog protein of human origin was obtained by PCR using the above reaction mixture as a template under conditions as follows. Sense and antisense primers for this PCR were obtained in usual manner based on the nucleotide sequence of a Desert hedgehog protein of mouse origin, which is reported by Y. Echelard et al. and registered in "GenBank®", a nucleic acid database established by National Institute of Health, USA, under the accession number "x76292"; they had respective nucleotide sequences of 5'-TGTGCTGCTTGGCACTCTTG-3' (SEQ ID NO:13) and 5'-CCGTGGCATTTCCCGGAAAG-3' (SEQ ID NO:14). Two microliters of 100-folds dilution of the reaction mixture of the above 5' RACE was placed in a fresh micro-reaction tube, then to which 3 µl of 10×PCR buffer, 1.8 µl of 25 mM $MgCl_2$, 0.6 µl of 10 mM dNTP mix, appropriate amounts of the sense and antisense primers, and sterile distilled water were added to give a final volume of 30 µl. After 0.3 µl of 5 units/µl Taq DNA polymerase was added to the tube, the mixture was subjected to an incubation at 94° C. for three minutes, 35 cycles of incubations at 94° C. for one minute, at 55° C. for one minute, and at 72° C. for one minute, and finally an incubation at 72° C. for 10 minutes, to effect PCR. The PCR products were subjected to 2%(w/v) agarose gel electrophoresis. A gel portion containing an about 600 bp-DNA band, stained with ethidium bromide, was excised and treated with "SUPREC™-01", a DNA purification tube commercialized by Takara Shuzo Co., Ltd.,Tokyo, Japan, to obtain 20 µl aqueous solution containing a DNA fragment.

A portion of the DNA fragment solution was sampled and manipulated with "pCR—SCRIPT SK(+) CLONING KIT", a DNA cloning kit commercialized by Stratagene Cloning Systems, California, USA, in accordance with the accompanying instructions to ligate the DNA fragment with "pCR-SCRIPT SK(+)", the plasmid vector in the kit. After the ligation, a portion of the reaction mixture was introduced by conventional transformation method into competent cells of *Escherichia coli* "JM101" strain, commercialized by Takara Shuzo Co., Ltd., Tokyo, Japan, which were then inoculated on plates of L agar medium containing 50 µg/ml ampicillin and cultured at 37° C. under standing conditions overnight. Some of the colonies formed were respectively suspended in 10 µl aliquotes of sterile distilled water. PCRs were conducted under the same conditions as described above in this Example except for using the suspensions as respective templates. Colonies which gave an about 600 bp-DNA on agarose gel electrophoresis were respectively inoculated to aliquotes of L broth medium containing 50 µg/ml ampicillin and cultured at 37° C. under shaking conditions overnight. From the resulting cultures, recombinant DNAs were collected by conventional alkali-sodium dodecyl sulfate (hereinafter, sodium dodesyl sulfate is abbreviated as "SDS") method. The recombinant DNAs were sequenced by dideoxy method. The DNA fragment in the recombinant DNAs contained the nucleotide sequence of SEQ ID NO:7.

Studying homology between thus-determined nucleotide sequence and other known nucleotide sequences, the nucleotide sequence determined in this Example exhibited a significant homology of about 89% to the nucleotide sequence of a mouse Desert hedgehog gene, registered in "GenBank®", a nucleic acid database by National Institute of Health, USA, under the accession number "X76292". This indicates that the DNA fragment of this Example encodes a human Desert hedgehog protein. The recombinant DNA obtained in this Example was named "pHuDHH/#20". In addition, the nucleotide sequence of SEQ ID NO:7, determined in this Example, was compared with the informations on structures and functions of known hedgehog proteins as described by M. Hammerschmidt et al., in *Trends in Genetics*, Vol.13, pp.14–21 (1997), leading to a conclusion that the sequence of nucleotides 19-546 of SEQ ID NO:7 encodes a mature form of a human Desert hedgehog protein and that the mature form of the protein can contain the amino acid sequence shown along with this nucleotide sequence, which is also shown in SEQ ID NO:1.

Example 1-2
Preparation of DNA Fragment and Recombinant DNA Encoding the Hedgehog Protein A recombinant DNA "pHuDHH/#20", obtained by the method in Example 1-1(c), was cleaved with restriction enzymes EcoR1 and NotI and subjected to 2%(w/v) agarose gel electrophoresis. From the agarose gel, a gel portion containing an about 600 bp-DNA band stained with ethidium bromide was excised and treated with "SUPREC™-01", a DNA purification tube commercialized by Takara Shuzo Co., Ltd., Tokyo, Japan, to collect and purify a DNA fragment. The purified DNA fragment was labelled with a radioisotope $^{32}P$ by using a DNA labelling kit, "MEGAPRIME™ DNA LABELLING SYSTEMS", commercialized by Amersham Corp., Div. Amersham International, Arlington Heights, USA, and manipulating in accordance with the accompanying instructions. Human fetal brain cDNA library constructed with a type of bacteriophage λgtll as a vector, commercialized by CLONTECH Laboratories, Inc., Palo Alto, Calif., USA, was screened by using the $^{32}P$-labelled DNA fragment as a probe. Cells of *Escherichia coli* strain "NM514" were infected with the cDNA library in usual manner, inoculated on plates of L agar medium, and cultured at 37° C. for 6–18 hours to form plaques. The formed plaques were transferred in usual manner to nylon membranes, which were then subjected to alkali-denaturalization, neutralization, and air-drying in usual manner. The air-dried membranes were immersed in a pre-hybridization solution, which contained 6×SSC, 5×Denhardt's solution, 0.5%(w/v) SDS, 50%(v/v) formamide, and 100 µg/ml denatured salmon sperm DNA, at 42° C. for 1–2 hours, and subsequently immersed in a fresh pre-hybridization solution with an appropriate amount of the $^{32}P$-labelled DNA fragment added as a probe and incubated at 42° C. for 16–20 hours to effect hybridization. After the hybridization, the membranes were washed with 2×SSC containing 0.1%(w/v) SDS at ambient temperature for 15 minutes and further washed with 0.2×SSC containing 0.1% (w/v) SDS at a temperature moderately increasing from 37° C. to 65° C. until background radioactivity was adequately reduced. Thereafter the membranes were subjected to autoradiography. From a plaque which gave a positive signal, a phage clone was collected and amplified in usual manner, and from the amplified phage a DNA clone was collected. The DNA clone was sequenced by dideoxy method using primers prepared based on the vector's nucleotide sequence. The DNA clone contained a partial nucleotide sequence as shown with 5'-GTATCCATGGCTCTCCTG-3' (SEQ ID NO:15). Compared with other known nucleotide sequences, the partial nucleotide sequence had a significant homology to a partial nucleotide sequence, containing translation initiation site, of a mouse Desert hedgehog gene registered in "GenBank®", a nucleic acid database by National Institute of Health, USA, under the accession number "X76292".

As sense and antisense primers for PCR, oligonucleotides with respective nucleotide sequences of 5'-GCCTCGAGGTATCCATGGCTCTCCTG-3' (SEQ ID NO:16), which contains the above-determined partial nucleotide sequence, and 5'-GCGCGGCCGCTCAGCCGCCCGCCCGGAC-3' (SEQ ID NO:17), which is complementary to the sequence of nucleotides 532-548 of SEQ ID NO:7, were prepared in usual manner. As a template one microliter portion of cDNAs solution, obtained by the methods in Examples 1-1(a) and 1-1(b), was placed in a micro-reaction tube, then to which 3 μl of 10×PCR buffer, 1.8 μl of 25 mM $MgCl_2$, 0.6 μl of 10 mM dNTP mix, appropriate amounts of the sense and antisense primers, and sterile distilled water were added to give a final volume of 30 μl. After 0.3 μl of 5 units/μl Taq DNA polymerase was added to thr tube, the mixture was subjected to an incubation at 94° C. for three minutes, 35 cycles of incubations at 94° C. for one minute, at 55° C. for one minute, and at 72° C. one minute, and finally an incubation at 72° C. for 10 minutes, to effect PCR. The PCR products were subjected to 2%(w/v) agarose gel electrophoresis. From the gel, a gel portion containing an about 600 bp-DNA band, stained with ethidium bromide, was excised and treated with "SUPREC™-01", a DNA purification tube commercialized by Takara Shuzo Co., Ltd., Tokyo, Japan, to obtain 20 μl aqueous solution containing a DNA fragment.

A small portion of the DNA fragment solution was sampled and manipulated with "pT7BLUE CLONING KIT", a DNA cloning kit commercialized by Takara Shuzo Co., Ltd., Tokyo, Japan, in accordance with the accompanying instructions to ligate the DNA fragment with "pT7BLUE", the plasmid vecotor in the kit. After the ligation, a portion of the reaction mixture was introduced by usual transformation method into competent cells of *Escherichia coli* strain "JM101", commercialized by Takara Shuzo Co., Ltd., Tokyo, Japan, which were then inoculated on plates of L agar medium containing 50 μg/ml ampicillin and cultured at 37° C. under standing conditions overnight. The formed colonies were respectively suspended in 10 μl aliquotes of sterile distilled water. Except for using the suspensions as respective templates, PCRs were conducted under the same conditions as in Example 1-1(c). Colonies which gave an about 600 bp-DNA band on agarose gel electrophoresis were respectively inoculated to aliquotes of L broth medium containing 50 μg/ml ampicillin and cultured at 37° C. under shaking conditions overnight. From the resulting cultures recombinant DNAs were collected by conventional alkali-SDS method. The recombinant DNAs were sequenced by dideoxy method. The DNA fragment in the recombinant DNAs contained the nucleotide sequence of SEQ ID NO:8, which can encode the amino acid sequence shown along with the nucleotide sequence.

The nucletotide sequence of SEQ ID NO:8 was compared with the nucleotide sequence of SEQ ID NO:7, determined in Example 1-1. The sequence of nucleotides 1-548 of SEQ ID NO:7 completely matched with the sequence of nucleotides 55-602 of SEQ ID NO:8. The results of this comparison and the comparison with the above-mentioned nucleotide sequence of a mouse Desert hedgehog gene revealed that: the nucleotide sequence of SEQ ID NO:8 encodes N-terminal region of a precursor form of a human Desert hedgehog protein; the sequence of nucleotides 7-72 of SEQ ID NO:8 encodes a signal peptide in a precursor form of the hedgehog protein; and the sequence of nucleotides 73-600 of SEQ ID NO:8 encodes a mature form of the hedgehog protein which contains the amino acid sequence of SEQ ID NO:1.

Example 1-3

Preparation of DNA Fragment and Recombinant DNA Encoding the Hedgehog Protein

As sense and antisense primers for PCR, oligonucleotides with respective nucleotide sequences of 5'-CGTGTCGGTCAAAGCTGATA-3' (SEQ ID NO:18) and 5'-ATGCATTCCAGTCGGCTGGA-3' (SEQ ID NO:19) were prepared in usual manner; the former sequence was identical to the sequence of nucleotides 501–520 of SEQ ID NO:7, and the latter sequence was based on the nucleotide sequence registered in "GenBank®", a nucleic acid database by National Institute of Health, USA, under the accession number "AA064660", which is of a human cDNA fragment similar to a 3'-terminal sequence for a mouse Desert hedgehog protein in a precursor form. As a template one microliter portion of cDNAs solution, obtained by the methods in Examples 1-1(a) and 1-1(b), was placed in a micro-reaction tube, then to which 3 μl of 10×PCR buffer, 1.8 μl of 25 mM $MgCl_2$, 0.6 μl of 10 mM dNTP mix, appropriate amounts of the above sense and antisense primers, and sterile distilled water were added to give a final volume of 30 μl. After 0.3 μl of 5 units/μl Taq DNA polymerase was added to the tube, the mixture was subjected to an incubation at 94° C. for three minutes, 35 cycles of incubations at 94° C. for one minute, at 55° C. for one minute, and at 72° C. one minute, and finally an incubation at 72° C. for 10 minutes to, effect PCR. The PCR products were subjected to 2%(w/v) agarose gel electrophoresis. From the gel, a gel potion containing an about 600 bp-DNA band, stained with ethidium bromide, was excised and treated with "SUPREC™-01", a DNA purification tube commercialized by Takara Shuzo Co., Ltd., Tokyo, Japan, to obtain 20 μl aqueous solution containing a DNA fragment.

A portion of the DNA fragment solution was sampled and manipulated with "pT7BLUE CLONING KIT", a DNA cloning kit commercialized by Takara Shuzo Co., Ltd., Tokyo, Japan, in accordance with the accompanying instructions to ligate the DNA fragment with "pT7BLUE", the plasmid vector in the kit. After the ligation, a portion of the reaction mixture was introduced by usual transformation method into competent cells of *Escherichia coli* strain "JM101", commercialized by Takara Shuzo Co., Ltd., Tokyo, Japan, which were then inoculated on plates of L agar medium containing 50 μg/ml ampicillin and cultured at 37° C. under standing conditions overnight. The formed colonies were respectively suspended in 10 μl aliquotes of sterile distilled water. Except for using the suspensions as respective templates and using the sense and antisense primers in this Example, PCRs were conducted under the same conditions as in Example 1-1(c). Colonies which gave an about 600 bp-DNA band on agarose gel electrophoresis were respectively inoculated to aliquotes of L broth medium containing 50 μg/ml ampicillin and cultured at 37° C. under shaking conditions overnight. From the resulting cultures recombinant DNAs were collected by conventional alkali-SDS method. The recombinant DNAs were sequenced by dideoxy method. The DNA fragment in the recombinant DNAs contained the nucleotide sequence of SEQ ID NO:9, which can encode the amino acid sequence shown along with the nucleotide sequence.

The nucleotide sequence of SEQ ID NO:9 was compared with the nucleotide sequence of SEQ ID NO:7, determined in Example 1-1. The sequence of nucleotides 501-548 of SEQ ID NO:7 completely matched with the sequence of nucleotides 1–48 of SEQ ID NO:9. In addition, the nucleotide sequence of SEQ ID NO:9 was compared with the informations on structure and function of known hedgehog proteins as described by M. Hammerschmidt et al., in *Trends in Genetics*, Vol.13, pp.14–21 (1997), revealing that the nucleotide sequence of SEQ ID NO:9 partially encodes a C-terminal region of a precursor form of a human Desert hedgehog protein.

Example 1-4
Preparation of DNA Fragment and Recombinant DNA Encoding the Hedgehog Protein Total RNAs in a weight of 1.5 μg, obtained by the method in Example 1-1(a), was placed in a micro-reaction tube, to which 2 μl of 5×reverse transcriptase buffer, 2 μl of DTT, one microliter of 10 mM dNTP mix, an appropriate amount of an oligonucleotide as an adaptor primer for a modified PCR method of 3' RACE with the nucleotide sequence of 5'-AAGGATCCGTCGACAAGCTTAATACGACGAATTC-TGGAG(T)$_{17}$-3' (SEQ ID NO:20) prepared in usual manner, and sterile distilled water were added to give a final volume of 29 μl. After admixed with one microliter of "Super-Script™ II RT", a reagent of reverse transcriptase commercialized by GIBCO BRL Life Technologies Inc., Rockville, Md., USA, the tube was allowed to stand at 37° C. for about 1.5 hours to effect a reaction of synthesizing cDNAs to poly(A)*RNAs 3'-terminal regions. Except for using a portion of the reaction mixture as a template and oligonucleotides with respective nucleotide sequences of 5'-GGCTTCGACTGGGTCTACTA-3' (SEQ ID NO:21) as a sense primer and 5'-AAGGATCCGTCGACAAG-3' (SEQ ID NO:22) as an antisense primer prepared in usual manner, a first step PCR was conducted under the same conditions as in Example 1-3; the sequence of the sense primer was identical to the sequence of nucleotides 460–479 of SEQ ID NO:7, and that of the antisense primer was based on the above adaptor primer. After the first step PCR, the reaction mixture was diluted with an appropriate amount of sterile distilled water. Except for using the dilution as a template and oligonucleotides with the respective nucleotide sequences of 5'-ATGCGCTTCGGCCAGCG-3' (SEQ ID NO:23) as a sense primer and 5'-GACAAGCTTAATACGAC-3' (SEQ ID NO:24) as an antisense primer, a second step PCR was conducted under the same conditions as in Example 1-3; the sequence of the sense primer was identical to the sequence of nucleotides 369-385 of SEQ ID NO:9, and that of the antisense primer was based on the nucleotide sequence of the above adaptor primer. After the second step PCR, the reaction mixture was diluted with an appropriate amount of sterile distilled water. Except for using the dilution as a template and oligonucleotides with the respective nucleotide sequences of 5'-GTTCGCGCCGCTCACCG-3' (SEQ ID NO:25) as a sense primer and 5'-TACGACGAATTCTGGAGT-3' (SEQ ID NO:26) as an antisense primer, a third step PCR was conducted under the same conditions as in Example 1-3; the sequence of the sense primer was identical to the sequence of nucleotides 424–440 of SEQ ID NO:9, and that of the antisense primer was based on the nucleotide sequence of the above adaptor primer. The third step PCR products were subjected to 2%(w/v) agarose gel electrophoresis. From the gel, a gel portion containing an about 750 bp-DNA band stained with ethidium bromide was excised and treated with "SUPREC™-01", a DNA purification tube commercialized by Takara Shuzo Co., Ltd., Tokyo, Japan, to obtain 20 μl aqueous solution containing a DNA fragment.

A portion of the DNA fragment solution was sampled and manipulated with "pT7BLUE CLONING KIT", a DNA cloning kit commercialized by Takara Shuzo Co., Ltd., Tokyo, Japan, in accordance with the accompanying instructions to ligate the DNA fragment with "pT7BLUE", the plasmid vector in the kit. After the ligation, a portion of the reaction mixture was introduced by usual transformation method into competent cells of *Escherichia coli* strain "JM101", commercialized by Takara Shuzo Co., Ltd., Tokyo, Japan, which were then inoculated on plates of L agar medium containing 50 μg/ml ampicillin and cultured at 37° C. under standing conditions overnight. The formed colonies were respectively suspended in 10 μl aliquotes of sterile distilled water. Except for using the suspensions as respective templates and using the sense and antisense primers in the third step PCR, PCRs were conducted under the same conditions as in Example 1-1(c). Colonies which gave an about 750 bp-DNA band on agarose gel electrophoresis were respectively inoculated to aliquotes of L broth medium containing 50 μg/ml ampicillin and cultured at 37° C. under shaking conditions overnight. From the resulting cultures recombinant DNAs were collected by alkali-SDS method. The recombinant DNAs were sequenced by dideoxy method. The DNA fragment in the recombinant DNAs contained the nucleotide sequence of SEQ ID NO:10, which can encode the amino acid sequence shown along with the nucleotide sequence.

The nucleotide sequence of SEQ ID NO:10 was compared with the nucleotide sequence of SEQ ID NO:9, determined in Example 1-3. The sequence of nucleotides 1–152 of SEQ ID NO:10 completely matched with the sequence of nucleotides 424–575 of SEQ ID NO:9. The results of this comparison and the comparison with the above-mentioned nucleotide sequence of a mouse Desert hedgehog gene revealed that the nucleotide sequence of SEQ ID NO:10 encodes a region containing the C-terminus of a precursor form of a human Desert hedgehog protein.

As described in Examples 1-1 to 1-4, the nucleotide sequences of SEQ ID NOs:7–10, determined in these Examples, were proved to be overlapping nucleotide sequences one another which partially encode a precursor form of a human Desert hedgehog protein; and the precursor protein can be wholly encoded by a DNA containing the nucleotide sequence of SEQ ID NO:6. In addition, these results elucidated that: a human Desert hedgehog protein can be in a precursor form which contains the amino acid sequence of SEQ ID NO:2 or 3 or in a mature form which contains the amino acid sequence of SEQ ID NO:1; such precursor protein can be encoded by a DNA containing the nucleotide sequence of SEQ ID NO:5 or 6, respectively; and such mature protein can be encoded by a DNA containing the nucleotide sequence of SEQ ID NO:4.

Example 2
Preparation of Transformant

Based on the nucleotide sequence determined in Example 1-1(c), which encodes a precursor form of a human Desert hedgehog protein, oligonucleotides with respective nucleotide sequences of 5'-CCCGGGAATTCATT-GCGGGCCGGGCCGGGGGCCG-3' (SEQ ID NO:27) as a sense primer and 5'-ACGATGAATTCTCAGCCGCC-CGCCCGGACCGCCA-3' (SEQ ID NO:28) as an antisense primer were prepared in usual manner. PCR was conducted under the same conditions as in Example 1-1(c) except for using the recombinant DNA "pHuDHH/#20" as a template, obtained by the method in Example 1-1(c), and the above sense and antisense primers. An about 600 bp-DNA amplified in this PCR was purified by 2%(w/v) agarose gel electrophoresis and treating with "SUPREC™-01", a DNA purification tube commercialized by Takara Shuzo Co., Ltd., Tokyo, Japan, in accordance with the accompanying instruction, to obtain 20 μl aqueous DNA solution. Two microliters portion of the DNA solution was sampled and subjected to a ligation reaction using T4 DNA ligase with "pCR™II", a plasmid vector for TA cloning commercialized by Invitrogen Corporation, San Diego, USA. A portion of the reaction mixture was introduced by usual transformation method into competent cells of *Escherichia coli* strain "TOP10F'", commercialized by Invitrogen Corporation, San Diego, USA, which were then inoculated on plates of L agar medium containing 50 μg/ml ampicillin and 50 μg/ml 5-bromo-4-chrolo-3-indolyl-β-D-galactoside and cultured at 37° C. under standing conditions. A white colony formed was inoculated to an aliquote of L broth medium containing 50 μg/ml ampicillin and cultured at 37° C. under shaking conditions overnight. From the resulting culture, a recombinant DNA was collected by alkali-SDS method. The recombinant DNA was treated with restriction enzyme EcoRI and subjected to 2%(w/v) agarose gel electrophoresis, on which an about 600 bp-DNA was separated, and it was then purified with "SUPREC™-01", a DNA purification tube commercialized by Takara Shuzo Co., Ltd, Tokyo, Japan.

A portion of the purified DNA solution was sampled and subjected to a ligation reaction in usual manner using T4 DNA ligase with plasmid vector "pGEX-2T", commercialized by Pharmacia Biotech, Inc., Uppsala, Sweden, which had been cleaved with EcoRI and dephosphorylated prior to use. A portion of the ligation reaction mixture was introduced by usual transformation method into competent cells prepared by applying the method in DNA cloning, Vol.1, edited by D. M. Glover, published by IRL press limited, Oxford, England (1985), pp.109–136, to *Escherichia coli* "BL21" strain, commercialized by Pharmacia Biotech, Inc., Uppsala, Sweden, which were then inoculated to plates of L agar medium containing 50 μg/ml ampicillin and cultured at 37° C. under standing conditions overnight. A colony formed was inoculated to an aliquote of L both medium containing 50 μg/ml ampicillin and cultured at 37° C. under shaking conditions overnight. From the resulting culture, a recombinant DNA was collected by alkali-SDS method. The recombinant DNA was confirmed by dideoxy method to contain the nucleotide sequence of SEQ ID NO:4, encoding the amino acid sequence of SEQ ID NO:1. The recombinant DNA and the transformant with the recombinant DNA introduced, thus obtained, were named "pHuDHH5'/pGEX-2T/#4-8" and "TAL#4-8/HuDHH", respectively. As shown in FIG. 1, in the recombinant DNA "pHuDHH5'/pGEX-2T/#4-8", the DNA with the nucleotide sequence of SEQ ID NO:4 encoding a mature form of a human Desert hedgehog protein and a termination codon were respectively located in the downstream and further downstream of a structural gene of glutathione S-transferase in the same frame with the gene, which was under the regulation of Tac promotor.

Example 3

Production of the hedgehog protein A transformant "TAL#4-8/HuDHH" obtained by the method in Example 2 was cultured in L broth medium containing 50 μg/ml ampicillin at 37° C. under shaking conditions overnight to obtain a seed culture. One milliliter of the seed culture was added to 100 ml of the same medium, freshly prepared in a 500 ml-Erlenmeyer flask, and cultured at 37° C. under shaking conditions while the absorbance at 600 nm was monitored. When the absorbance reached a value of 0.5, 0.1 ml of 100 mM isopropylthio-β-D-galactoside was added to the culture. After further cultivation at 37° C. for 3.5 hours, the cells were collected from the culture by centrifugation. The cells were washed with PBS, suspended in 5 ml of fresh preparation of PBS, and disrupted with ultrasonication in usual manner. After the cell-disruptant was centrifuged, the formed supernatant was collected.

The supernatant was added to "GLUTATHIONE SEPHAROSE 4B BEADS", a preparation of sepharose beads linked to glutathione, commercialized by Pharmacia Biotech, Inc., Uppsala, Sweden, and incubated at ambient temperature for 30 minutes. After centrifugation of the mixture and discard of the resulting supernatant, the beads were washed twice with PBS. To the beads, an appropriate amount of 50 mM Tris-HCl buffer (pH 7.5) containing 2.5 mM CaCl$_2$ and 150 mM NaCl was added, and admixed with 10 units of thrombin, commercialized by Ito Ham Co., Ltd., Nishinomiya, Japan, per one milligram of the proteinaceous components. The mixture was incubated at ambient temperature for 16 hours. The mixture was centrifuged to collect a supernatant, which was then admixed with an appropriate amount of "ANTITHROMBIN AGAROSE", commercialized by Sigma Chemical Company, St. Louis, Mo., USA, and centrifuged. The resulting supernatant was added to "HEPARIN AGAROSE", commercialized by Sigma Chemical Company, St. Louis, Mo., USA, previously equilibrated with equilibration buffer (PBS containing 1.0 mM DTT and 0.2 mM phenylmethanesulfonyl fluoride), and incubated at ambient temperature for 30 minutes. The mixture was admixed with an appropriate amount of equilibration buffer and centrifuged, and the resulting supernatant was discarded. To the remaining components an appropriate amount of 650 mM NaCl was added, and the resulting mixture was centrifuged to collect a supernatant. These treatments, i.e., addition of 650 mM NaCl, centrifugation, and collection of a supernatant, were additionally applied twice to the remaining components, and the supernatants thus obtained were pooled.

A portion of the pooled liquid was subjected to SDS-polyacrylamide gel electrophoresis (hereinafter, abbreviated as "SDS-PAGE") in the presence of a reducing agent, in accordance with the method by U. K. Laemli, in Nature, Vol.227, pp.680–685 (1970). As molecular weight markers "SDS-PAGE STANDARDS, LOW RANGE", containing six proteins with distinctive molecular weights of 14,400–97,400 daltons, commercialized by Bio-rad Laboratories Inc., Richmond, USA, was used. Main bands were observed at positions corresponding to molecular weights of about 22,000±2,000 daltons and about 18,000±2,000 daltons. Reference 1 was conducted in the same manner as in this Example except for using *Escherichia coli* "BL21" strain in place of the transformant "TAL#4-8/HuDHH", giving no remarkable band on SDS-PAGE. Reference 2 was conducted in the same manner as this Example except for using *Escherichia coli* "BL21" strain transformed with the plasmid vector "pGEX-2T" in place of the transformant "TAL#4-8/HuDHH", giving no remarkable band on SDS-PAGE.

The molecular weight of a human Desert hedgehog protein in a mature form which has the amino acid sequence of SEQ ID NO:1 is calculated to be 19,747. According to this Example, the objective protein is usually generated in a form with a peptide as shown by Gly-Ser-Pro-Gly-Ile-His- (SEQ ID NO:29) added to the N-terminus and collected. The molecular weight of a protein that has the amino acid sequence of SEQ ID NO:1 and Gly-Ser-Pro-Glylle-His- (SEQ ID NO:29), which is added to the N-terminus of SEQ ID NO:1, is calculated to be 20,296. These indicate that the protein obtained by the method in this Example which gave a molecular weight of 22,000±2,000 daltons on SDS-PAGE is a type of the present hedgehog protein, containing the amino acid sequence of SEQ ID NO:1. The other protein obtained by the method in this Example, which gave a molecular weight of 18,000±2,000 daltons on SDS-PAGE, is considered to be a degradation product of the hedgehog protein formed during the process of this Example. These results mean that the process of this invention satisfactorily produces a human Desert hedgehog protein of this invention.

Example 4
Production of Monoclonal Antibody

Example 4-1
Preparation of Immunogen

Example 4-1(a)
Preparation of Transformant Introduced with DNA that Encodes Immunogen A549 cells, ATCC CCL-185, an established cell line derived from a human lung carcinoma, were suspended in RPMI-1640 medium (pH 7.2) supplemented with 10%(v/v) fetal bovine serum and proliferated in usual manner at 37° C. in a 5%(v/v) $CO_2$ incubator while scaling up the culture. After the cell density reached a desired level, proliferated cells were collected. The cells were manipulated with "ULTRASPEC™ RNA", similarly as in Example 1-1(a), to obtain an aqueous solution containing total RNAs of A549 cells. By applying usual RT-PCR method to the total RNAs, a DNA fragment encoding a mature form of a human Sonic hedgehog protein was amplified. As the sense and antisense primers in this RTPCR, oligonucleotides with respective nucleotide sequences of 5'CCCGGGAATT-CATTGCGGACCGGGCAGGGGGTT-3' (SEQ ID NO:30) and 5'ACGATGAATTCTCAGCCTCCCGATTTGGCCGC-3' (SEQ ID NO:31), prepared in usual manner based on the nucleotide sequence of a human Sonic hedgehog gene, reported by V. Marigo et al. and registered in "GenBank®", a nucleic acid database by National Institute of Health, USA, under the accession number "L38518", were used. The amplified DNA fragment was collected by treating the RT-PCR products with "SUPREC™-01", as in Example 1-1(c). Similarly as in Example 1-1(c), the DNA fragment was ligated with plasmid vector "PCRIII" and introduced into *Escherichia coli* "TOP10F'" strain, the obtained transformant was cultured, and from the resulting culture a recombinant DNA was collected by alkali-SDS method. The recombinant DNA was sequenced by dideoxy method, confirming that it contained the nucleotide sequence of SEQ ID NO:11, encoding a human Sonic hedgehog protein in a mature form.

Similarly as in Example 2, an aliquot of the recombinant DNA was cleaved with restriction enzyme EcoRI to form an about 600 bp-DNA, which was then collected by treating with "SUPREC™-01", ligated with plasmid vector "pGEX-2T", and introduced into *Escherichia coli* "BL21" strain. The obtained transformant was cultured, and from the resulting culture a recombinant DNA was collected by alkali-SDS method. The recombinant DNA was sequenced by dideoxy method, confirming that it contained a DNA with the nucleotide sequence of SEQ ID NO:11 and a termination codon, which are respectively located in the downstream and further downstream of a structural gene of glutathione S-transferase in the same frame under the regulation of Tac promotor. The recombinant DNA and the transformant with the recombinant DNA introduced, thus obtained, were named "pHuSHH/pGEX-2T/#3-1" and "TAL#3-1/HuSHH", respectively.

Example 4-1(b)
Preparation of Immunogen using Transformant

Similarly as in Example 3, the transformant "TAL#3-1/HuSHH" obtained by the method in Example 4-1(a) was cultured, the proliferated cells were collected from the culture, and a supernatant of the cell-disruptant was obtained. By applying the methods using "GLUTATHIONE SEPHAROSE 4B BEADS", thrombin, "ANTITHROMBIN AGAROSE" and "HEPARIN AGAROSE" in Example 3 to the supernatant, an aqueous solution containing a protein derived from "TAL#3-1/HuSHH" was obtained, and analyzed by SDS-PAGE; a main band was observed at a position corresponding to a molecular weight of 22,000±2,000. The molecular weight of a mature form of a human Sonic hedgehog protein which has the amino acid sequence shown along with SEQ ID NO:11 is calculated to be 19,747. According to this Example, the objective protein is usually generated in a form with a peptide as shown by Gly-SerPro-Gly-Ile-His-(SEQ ID NO:29) added to the N-terminus and collected. These indicate that the protein obtained in this Example is a human Sonic hedgehog protein with a satisfactory purity. Thus, a purified preparation of a human Sonic hedgehog protein as an immunogen was obtained.

Example 4-2
Preparation of Hybridoma

Seven-week-old BALB/c mice were intraperinoneally injected with a purified preparation of a human Sonic hedgehog protein, obtained by the method in Example 4-1(b), in a dose of 100 µg/body together with complete Freund adjuvant in usual manner. Two weeks later, the above injection was repeated, and then the mice were injected with incomplete Freund adjuvant three times with one-week interval. On the fourth day after the final injection, spleens were extracted from the mice and dispersed to obtain splenocytes.

The splenocytes and SP2/0-Ag14 cells, ATCC CRL-1581, derived from mouse, were co-suspended in a serum-free RPMI 1640 medium, which had been warmed prior to use to 37° C., to give respective cell densities of $3 \times 10^4$ and $1 \times 10^4$ cells/ml, and then centrifuged to collect a precipitate. To the precipitate, one milliliter of a serum-free RPMI 1640 medium (pH 7.2) containing 50%(w/v) polyethylene glycol with an average molecular weight of about 15,000 daltons was dropped over one minute, and the resulting mixture was incubated at 37° C. for one minute. A serumfree RPMI 1640 medium (pH 7.2) was further dropped to the mixture to give a final volume of 50 ml, which was then centrifuged to collect a precipitate. The precipitate was suspended in HAT medium, distributed to wells of 96-well microplates in a volume of 200 µl/well, and incubated at 37° C. for a week to select hybridomas.

Antibodies secreted in culture supernatants in the wells were tested for a reactivity with a Sonic hedgehog protein, obtained in Example 4-1(b), by conventional enzyme-immunoassay to select hybridomas which exhibited the reactivity. The antibodies secreted in the culture supernatants of the selected hybridomas were further tested for another reactivity with the hedgehog protein of this invention, obtained in Example 3, by conventional enzyme-immunoassay to select hybridomas which additionally exhibited the reactively. Thereafter, the finally selected hybridomas were repeatedly subjected to limiting dilution method, resulting in obtaining hybridoma clones capable of producing the monoclonal antibody of this invention which were named "SH2-3", "SH2-21", and "SH2-260".

Example 4-3
Production of Monoclonal Antibody

Hybridomas "SH2-3", "SH2-21", and "SH2-260" obtained in Example 4-2 were separately suspended to give a cell density of $1 \times 10^6$ cells/ml each in aliquotes of RPMI 1640 medium (pH 7.2) supplemented with 5%(v/v) fetal bovine serum, and cultured at 37° C. in a 5%(v/v) $CO_2$ incubator while scaling up the culture. After the cell densities reached a desired level, the hybridomas were peritoneally injected in a dose of $1 \times 10^7$ cells/body to eight-week-old BALB/c mice which had been peritoneally injected with 0.5 ml/body "PRISTANE", a reagent of 2,6,10,14-tetramethylpentadecane commercialized by Aldrich Chemical Co., Inc., Milwaukee, USA, and the mice were fed for a week in usual manner.

From the respective lines of mice, ascites were collected and threefold diluted with PBS. To the dilutions, ammonium sulfate was added to give 50% saturation. The resulting mixture was allowed to stand at 4° C. for 24 hours and then centrifuged to collect precipitates. The precipitates were dialyzed against 20 mM $KH_2PO_4$ (pH 6.7) at 4° C. overnight, and then charged to columns of hydroxyapatite, pre-equilibrated with 20 mM $KH_2PO_4$ (pH 6.7). Through the columns, running $KH_2PO_4$ (pH 6.7) solution with increasing concentration from 20 to 300 mM in a linear gradient manner resulted in obtaining aqueous solutions of "SH2-3 mAb", "SH2-21 mAb", and "SH2-260 mAb", the monoclonal antibodies of this invention. The yields were about 5 mg/mouse each. Analyzing in usual manner, all of the monoclonal antibodies belonged to a class of $IgG_1$.

Example 5

Western Blotting

One microgram of a Desert hedgehog protein, obtained by the method in Example 3, was subjected to SDS-PAGE with 15%(w/v) gel in the presence of a reducing agent. In parallel, 50 ng of a Sonic hedgehog protein, obtained by the method in Example 4-1(b), was subjected to SDS-PAGE with 13% (w/v) gel in the presence of a reducing agent. In usual manner, proteinaceous components in the gels were transferred to nitrocellulose membranes, which were then immersed in "BLOCK ACES™", an immobilizing agent commercialized by Dainippon Pharmaceutical Co., Ltd., Osaka, Japan, to effect blocking. The membranes were immersed in PBS containing 20 µg/ml "SH2-3 mAb", monoclonal antibody obtained by the method in Example 4-3, 10%(v/v) "BLOCK ACE™, and 0.1%(v/v) "TWEEN20", a detergent commercialized by City Chemical Corp., New York, U.S.A., for one hour; and washed with PBS containing 0.1%(v/v) "TWEEN 20" to remove excessive antibodies. Thereafter, the nitrocellulose membranes were reacted for one hour in PBS containing 0.1%(v/v) sheep anti-mouse immunoglobulin antibody labelled with horseradish peroxidase, 10%(v/v) "BLOCK ACE™", and 0.05%(v/v) "TWEEN 20"; washed with PBS containing 0.1%(v/v) "TWEEN 20"; and color-developed by using "ECL™ KIT", a kit for color development commercialized by Amersham International plc, Buckinghamshire, UK. The molecular weight markers used were "SDS-PAGE STANDARDS, LOW RANGE", containing six proteins having distinctive molecular weights of 14,400–97,400 daltons, commercialized by Bio-rad Laboratories Inc., Richmond, USA. The results are in FIG. 2.

Figure 2:
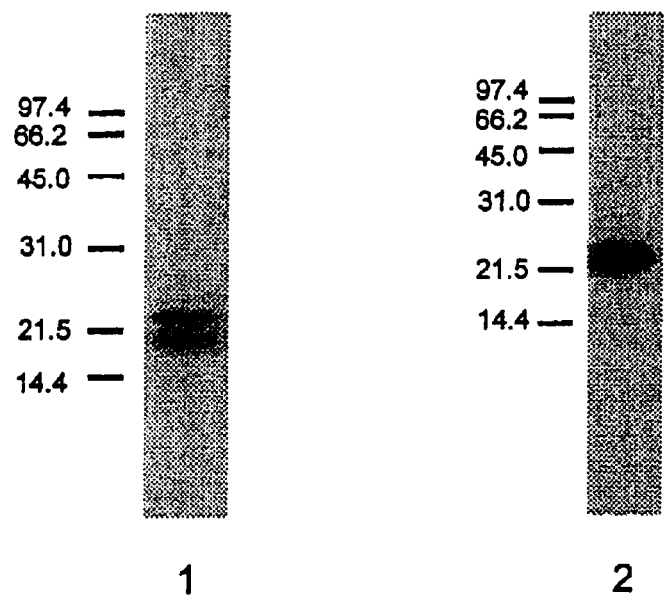
FIG. 2 is a half tone image of gel electrophoresis given on a display, visualized by Western blotting as the detection method using the monoclonal antibody of this invention.

In FIG. 2, on Lane 1, the band corresponding to a molecular weight of 22,000±2,000 is of the hedgehog protein of this invention, and the other band, corresponding to a molecular weight of 18,000±2,000, is of the degradation product of the hedgehog protein formed during the process in Example 3. In FIG. 2, on Lane 2, the band corresponding to a molecular weight of 22,000±2,000 is of a human Sonic hedgehog protein, obtained by the method in Example 4-1(b).

Another Western blotting which was conducted in the same manner as above except for using a monoclonal antibody "SH2-21 mAb", obtained by the method in Example 4-3, in place of the monoclonal antibody "SH2-3 mAb", giving similar results as above. These results indicate that the monoclonal antibodies, according to this invention, well recognized not only a human Sonic hedgehog protein but also a human Desert hedgehog protein.

Example 6

Enzyme-Immunoassay

Monoclonal antibodies "SH2-3 mAb" and "SH2-260 mAb", obtained by the method in Example 4-3, were co-diluted in PBS to give a concentration of 10 µg/ml each, the resulting solution was distributed to wells of 96-well microplates in a volume of 100 µl/well. The microplates were incubated at ambient temperature. From the microplates the solution was removed, and PBS containing 1%(w/v) bovine serum albumin was distributed to the wells in a volume of 200 µl/well. Then the microplates were allowed to stand at 4° C. overnight. In parallel, a human Desert hedgehog protein, obtained by the method in Example 3, and a human Sonic hedgehog protein, obtained by the method in Example 4-1(b), were separately diluted with PBS to give desired different concentrations. After removing the solution from the microplates, and the respective hedgehog protein solutions were added to the wells and reacted at ambient temperature for one hour. The microplates were washed with PBS containing 0.05%(v/v) "TWEEN 20", and added with a rabbit anti-hedgehog protein antiserum 500-fold diluted with PBS in a volume of 100 µl/well. The antiserum used in this Example was obtained by immunizing rabbits with a human Sonic hedgehog protein, obtained by the method in Example 4-1(b), and collecting serum from the rabbits in usual manner.

After the reaction with the antiserum, the microplates were washed with PBS containing 0.05%(v/v) "TWEEN 20" and added with a horseradish peroxidase-labelled donkey anti-rabbit immunoglobulin antibody, commercialized by Amersham International plc, Buckinghamshire, UK, which had been 1000-fold diluted with PBS, followed by allowing the microplates to stand at ambient temperature for one hour. The microplates were washed with PBS containing 0.05%(v/v) "TWEEN 20". Thereafter, in usual manner, a mixture solution of o-phenylene diamine as a substrate and $H_2O_2$ was added to the wells in a volume of 100 µl/well followed by an incubation at ambient temperature for 15 minutes to effect enzyme reaction, and the reaction was terminated by 2N $H_2SO_4$ added. Intensities of colors in the wells developed by the reaction were estimated by measuring the absorbance at 492 nm. The results are in FIG. 3.

Figure 3:
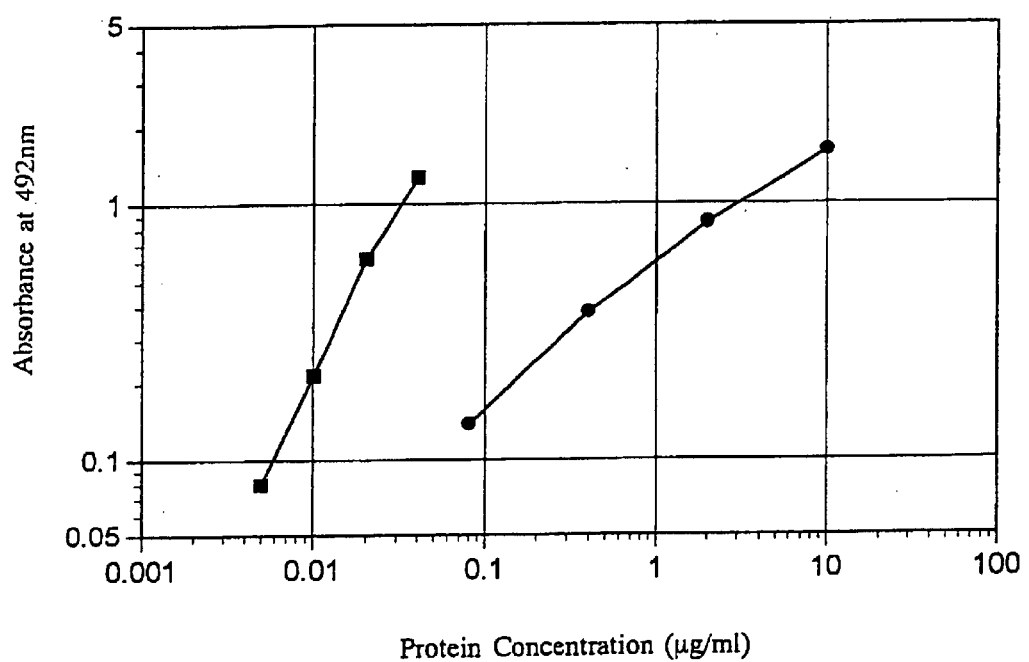
FIG. 3 shows the results of detecting the hedgehog protein by an enzyme-immunoassay as the detection method using the monoclonal antibody of this invention.

The results in FIG. 3. indicate that the method for detecting, according to this invention, well detected not only a human Sonic hedgehog protein but also a human Desert hedgehog protein.

As described above, this invention was established based on the finding of a novel hedgehog protein, i.e., a Desert hedgehog protein of human origin. The hedgehog protein of this invention is useful in establishment of a hybridoma capable of producing a monoclonal antibody that recognizes the protein. The hedgehog protein of this invention has efficacy in treatment and prevention of susceptive diseases to the hedgehog protein. The monoclonal antibody is useful in purification and detection of human Desert hedgehog protein because the antibody recognizes the hedgehog protein. The monoclonal antibody has efficacy in treatment, prevention, and diagnosis of diseases relating to excessive production of the hedgehog protein in living bodies. In addition to these effectiveness, the protein, DNA, and monoclonal antibody of this invention are extremely useful in elucidation of the process of exhibiting hereditary morphological abnormalities in humans. The process of this invention does satisfactorily produce the hedgehog protein.

This invention, which exhibits these remarkable effects, would be very significant and contributive to the art.

While there has been described what is at present considered to be the preferred embodiments of the present invention, it will be understood the various modifications may be made therein, and it is intended to cover in the appended claims all such modifications as fall within the true spirits and scope of the invention.

---

What is claimed is:

1. An isolated DNA which encodes a desert hedgehog protein of human origin having the amino acid sequence of SEQ ID NO:1, or an isolated DNA complementary thereto.

2. An isolated DNA which encodes a desert hedgehog protein of human origin having the amino acid sequence of SEQ ID NO:2, or an isolated DNA complementary thereto.

3. An isolated DNA which encodes a desert hedgehog protein of human origin having the amino acid sequence of SEQ ID NO:3, or an isolated DNA complementary thereto.

4. The DNA of claim 1, and which contains the whole of the nucleotide sequence of SEQ ID NO:4.

5. The DNA of claim 2, which contains the whole of the nucleotide sequence of SEQ ID NO: 5.

6. An isolated DNA which encodes a desert hedgehog protein of human origin having the nucleotide sequence of SEQ ID NO:5, or an isolated DNA complementary thereto.

7. An isolated DNA which encodes a desert hedgehog protein of human origin having the nucleotide sequence of SEQ ID NO:6, or an isolated DNA complementary thereto.

8. The DNA of any one of claims 4, 6, 7, 1, 2 or 3, which is inserted into an autonomously replicable vector.

9. A transformed cell obtained by introducing the DNA of claim 8, into an appropriate host cell derived from a microbe, plant or animal.

10. A process for producing a desert hedgehog protein of human origin, which comprises culturing the transformed cell of claim 9 to generate said desert hedgehog protein of human origin, and collecting the generated desert hedgehog protein of human origin.

11. The process of claim 10, wherein the generated desert hedgehog protein of human origin is collected by one or more methods selected from the group consisting of salting out, dialysis, filtration, concentration, fractional precipitation, ion-exchange chromatography, gel filtration chromatography, adsorption chromatography, isoelectric focusing chromatography, hydrophobic chromatography, reversed phase chromatography, affinity chromatography, gel electro-phoresis and isoelectric focusing gel electro-phoresis.

12. The process of claim 10, wherein the generated desert hedgehog protein of human origin is collected through immunoaffinity chromatography using a monoclonal antibody that recognizes a desert hedgehog protein of human origin.

\* \* \* \* \*